(12) United States Patent
Abouabdellah et al.

(10) Patent No.: US 7,781,590 B2
(45) Date of Patent: Aug. 24, 2010

(54) PIPERIDINYLALKYLCARBAMATE DERIVATIVES, METHODS FOR THEIR PREPARATION AND THE THERAPEUTIC USE THEREOF AS FATTY ACID AMIDO HYDROLASE ENZYME INHIBITORS

(75) Inventors: Ahmed Abouabdellah, Thiais (FR); Antonio Almario Garcia, Chatenay Malabry (FR); Christian Hoornaert, Antony (FR); Jean Jeunesse, Paris (FR)

(73) Assignee: Sanofi-Aventis, Paris (FR)

( * ) Notice: Subject to any disclaimer, the term of this patent is extended or adjusted under 35 U.S.C. 154(b) by 1038 days.

(21) Appl. No.: 11/465,825

(22) Filed: Aug. 21, 2006

(65) Prior Publication Data

US 2007/0021403 A1    Jan. 25, 2007

Related U.S. Application Data

(63) Continuation of application No. PCT/FR2005/00452, filed on Feb. 25, 2005.

(30) Foreign Application Priority Data

Feb. 26, 2004    (FR) .................................. 04 01952

(51) Int. Cl.
  *C07D 421/00* (2006.01)
  *C07D 211/26* (2006.01)
(52) U.S. Cl. ...................................... 546/209; 546/229
(58) Field of Classification Search ................. 546/209, 546/229
See application file for complete search history.

(56) References Cited

U.S. PATENT DOCUMENTS 4,539,323 A    9/1985    Mentrup et al.

FOREIGN PATENT DOCUMENTS

| WO | WO 99/26584   | 6/1999  |
| WO | WO 02/087569  | 11/2002 |
| WO | WO 03/065989  | 8/2003  |
| WO | WO 2004/020430| 3/2004  |
| WO | WO 2004/067498| 8/2004  |
| WO | WO 2004/099176| 11/2004 |
| WO | WO 2005/033066| 4/2005  |

OTHER PUBLICATIONS

Shapiro, S.L., et. al., Aminoalkylamides and Oxazolidinediones, Journal of the American Chemical Society, vol. 81, No. 12, (1959) pp. 3083-3088.

*Primary Examiner*—D. Margaret Seaman
*Assistant Examiner*—Nizal S Chandrakumar
(74) *Attorney, Agent, or Firm*—Balaram Gupta

(57) ABSTRACT

The present invention comprises peridinylalkylcarbamate derivatives, methods for their preparation and the therapeutic use thereof as fatty acid amido hydrolase (FAAH) enzyme inhibitors. These derivatives exert various pharmacological activities by interacting, inter alia, with cannabinoid and vanilloid receptors. By inhibiting the metabolic activity of the FAAH enzyme, compounds often responsible for the onset of a large variety of diseases and other pathological conditions are not generated and the incidence of the disease is greatly reduced.

9 Claims, No Drawings

PIPERIDINYLALKYLCARBAMATE DERIVATIVES, METHODS FOR THEIR PREPARATION AND THE THERAPEUTIC USE THEREOF AS FATTY ACID AMIDO HYDROLASE ENZYME INHIBITORS

CROSS-REFERENCE TO RELATED APPLICATIONS

This application is a continuation of International Application No. PCT/FR2005000452 filed on Feb. 25, 2005 which is incorporated herein by reference in its' entirety which also claims the benefit of priority of French Patent Application No. 04/01952 filed on Feb. 26, 2004.

FIELD OF THE INVENTION

The present invention relates generally to enzyme inhibitors and their use in the treatment and therapy of a wide variety of diseases and degenerative conditions. More particularly, the present invention is directed towards the use of piperidinylalkylcarbamate derivatives, processes for their preparation and the use thereof as fatty acid amido hydrolase inhibitors in the treatment of arthritis, heart disease, cancer and the like and to their application in a wide variety of therapeutic regimens.

BACKGROUND OF THE INVENTION

Phenylalkylcarbamate derivatives, dioxane-2-alkylcarbamate derivatives and piperidinyl- and piperazinyl-alkylcarbamate derivatives, are described respectively in the documents WO 2004/067498 A, WO 2004/020430 A and WO 2004/099176, as being useful inhibitors of the enzyme fatty acid amido hydrolase. (FAAH). These references and their teachings are hereby incorporated by reference herein.

The fatty acid amido hydrolase enzyme (FAAH) (*Chemistry and Physics of Lipids*, (2000), 108, 107-121) catalyses the hydrolysis of endogenous derivatives of amides and of esters of various fatty acids such as N-arachidonoylethanolamine (anandamide), N-palmitoylethanolamine, N-oleoyl-ethanolamine, oleamide or 2-arachidonoylglycerol. These derivatives exert various pharmacological activities by interacting, inter alia, with cannabinoid and vanilloid receptors.

The compounds of the present invention block this degradation pathway and increase the tissue level of these endogenous substances. They can be used in this respect in the prevention and treatment of pathologies in which endogenous cannabinoids and/or any other substrates metabolized by the FAAH enzyme are involved.

SUMMARY OF THE INVENTION

The present invention comprises piperidinylalkylcarbamate derivatives, methods for their preparation and the therapeutic use thereof as fatty acid amido hydrolase (FAAH) enzyme inhibitors. These derivatives exert various pharmacological activities by interacting, inter alia, with cannabinoid and vanilloid receptors. By inhibiting the metabolic activity of the FAAH enzyme, compounds often responsible for the onset of disease and other pathological conditions are not generated and the incidence of the disease is greatly reduced.

DETAILED DISCLOSURE OF THE INVENTION

Diseases and pathological conditions that often result from the presence of these compounds that are generated by the metabolic activity of the fatty acid amido hydrolase enzyme include but are not limited to, for example, the following:
pain, especially acute or chronic pain of neurogenic type: migraine, neuropathic pain, including forms associated with the herpes virus and with diabetes;
acute or chronic pain associated with inflammatory diseases: arthritis, rheumatoid arthritis, osteoarthritis, spondylitis, gout, vasculitis, Crohn's disease, irritable bowel syndrome;
acute or chronic peripheral pain; dizziness, vomiting, nausea, especially those subsequent to chemotherapy;
eating disorders, especially anorexia and cachexia of various kinds;
neurological and psychiatric pathologies: shaking, dyskinesia, dystonia, spasticity, obsessive-compulsive behaviours, Tourette's syndrome, all forms of depression and anxiety of any kind and cause, mood disorders, psychoses; acute and chronic neurodegenerative diseases: Parkinson's disease, Alzheimer's disease, senile dementia, Huntington's chorea, lesions associated with cerebral ischemia and with cranial and medullary trauma; epilepsy;
sleep disorders, including sleep apnoea;
cardiovascular diseases, especially hypertension, cardiac arrhythmias, arteriosclerosis, heart attack, cardiac ischemias; renal ischemia; cancers: benign skin tumours, papillomas and brain tumours, prostate tumours, brain tumours (glioblastomas, medulloepitheliomas, medulloblastomas, neuroblastomas, tumours of embryonic origin, astrocytomas, astroblastomas, ependyomas, oligodendrogliomas, plexus tumour, neuroepitheliomas, epiphysial tumour, ependymoblastomas, malignant meningiomas, sarcomatoses, malignant melanomas, schwannomas); disorders of the immune system, especially autoimmune diseases: psoriasis, lupus erythematosis, diseases of the connective tissue or collagen diseases, Sjögren's syndrome, ankylosing spondylarthritis, undifferentiated spondylarthritis, Behcet's disease, haemolytic autoimmune anaemias, multiple sclerosis, amyotrophic lateral sclerosis, amyloses, transplant rejection, diseases affecting the plasmocytic line;
allergic diseases: immediate or delayed hypersensitivity, allergic rhinitis or conjunctivitis, hypersensitivity, allergic rhinitis or conjunctivitis, contact dermatitis; parasitic, viral or bacterial infectious diseases: AIDS, meningitis; inflammatory diseases, in particular joint diseases: arthritis, rheumatoid arthritis, osteoarthritis, spondylitis, gout, vasculitis, Crohn's disease, irritable bowel syndrome; osteoporosis;
eye conditions: ocular hypertension, glaucoma;
pulmonary conditions: diseases of the respiratory tract, bronchospasm, coughing, asthma, chronic bronchitis, chronic obstruction of the respiratory tract gastrointestinal diseases: irritable bowel syndrome, inflammatory intestinal disorders, ulcers, diarrhea; urinary incontinence and bladder inflammation.

There is still a need to find and to develop pharmaceutical actives and composition formulations containing the same which inhibit the enzyme fatty acid amido hydrolase (FAAH) and consequently the diseases believed to be a result of the enzymes' metabolic action. Any one of the compounds of the present invention achieve this goal.

The compounds of the invention are of the general formula (I)

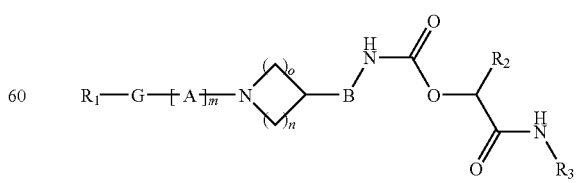

in which
m represents an integer from 1 to 4;

n represents an integer 1, 2 or 3;
o an integer 1 or 2;
A is selected from one or more groups X, Y and/or Z;
  X represents a methylene group optionally substituted by one or two $C_{1-6}$ alkyl, $C_{3-7}$ cycloalkyl or $C_{3-7}$ cycloalkyl-$C_{1-3}$ alkylene groups;
  Y represents either a $C_2$ alkenylene group optionally substituted by one or two $C_{1-6}$ alkyl, $C_{3-7}$ cycloalkyl or $C_{3-7}$ cycloalkyl-$C_{1-3}$ alkylene groups, or a $C_2$ alkynylene group;
  Z represents a group of formula:

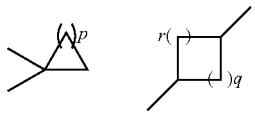

p represents an integer from 1 to 5;
  q and r represent integers and are defined such that r+q is a number from 1 to 5;
B represents a covalent bond or a $C_{1-6}$ alkylene group;
G represents a covalent bond, an oxygen or sulphur atom or a —CH(OH)—, CO, SO or $SO_2$ group;
$R_1$ represents a group $R_4$ optionally substituted by one or more groups $R_5$ and/or $R_6$;
  $R_4$ represents a group selected from a furanyl, pyrrolyl, thienyl, oxazolyl, isoxazolyl, thiazolyl, isothiazolyl, imidazolyl, pyrazolyl, thiadiazolyl, isothiadiazolyl, oxadiazolyl, thiadiazolyl, triazolyl, tetrazolyl, phenyl, pyridinyl, pyridazinyl, pyrimidinyl, pyrazinyl, triazinyl, naphthalenyl, quinolinyl, tetrahydroquinolinyl, isoquinolinyl, tetrahydroisoquinolinyl, phthalazinyl, quinazolinyl, quinoxalinyl, cinnolinyl, naphthyridinyl, imidazopyrimidinyl, thienopyrimidinyl, benzofuranyl, dihydrobenzofuranyl, benzothienyl, dihydrobenzothienyl, benzimidazolyl, benzoxazolyl, benzisoxazolyl, benzothiazolyl, benzisothiazolyl, indolyl, isoindolyl, indazolyl, pyrrolopyridinyl, furopyridinyl, dihydrofuropyridinyl, thienopyridinyl, dihydrothienopyridinyl, imidazopyridinyl, pyrazolopyridinyl, oxazolopyridinyl, isoxazolopyridinyl, thiazolopyridinyl;
  $R_5$ represents a halogen atom, a cyano, nitro, hydroxyl, $C_{1-6}$ alkyl, $C_{1-6}$ alkoxy, $C_{1-6}$ thioalkyl, $C_{1-6}$ fluoroalkyl, $C_{1-6}$ fluoroalkoxy, $C_{1-6}$ fluorothioalkyl, $C_{3-7}$ cycloalkyl or $C_{3-7}$ cycloalkyl-$C_{1-3}$ alkylene group or a group $NR_7R_8$, $NR_7COR_8$, $NR_7CO_2R_8$, $NR_7SO_2R_8$, $COR_7$, $CO_2R_7$, $CONR_7R_8$, $SO_2R_7$, $SO_2NR_7R_8$ or —O—($C_{1-3}$ alkylene)-O—;
  $R_6$ represents a phenyl, phenyloxy, benzyloxy, pyridinyl, pyrazinyl, pyridazinyl, pyrimidinyl or pyrimidinyloxy group; it being possible for the group or groups $R_6$ to be substituted by one or more groups $R_5$ identical to or different from one another;
  $R_7$ and $R_8$ represent independently of one another a hydrogen atom or a $C_{1-6}$ alkyl group, or, with the atom or atoms which carry them, form a ring selected from an azetidine, pyrrolidine, piperidine, morpholine, thiomorpholine, azepine or piperazine ring, this ring being optionally substituted by a $C_{1-6}$ alkyl or benzyl group;
$R_2$ represents a hydrogen atom or a $C_{1-6}$ alkyl group;
$R_3$ represents a hydrogen atom or a $C_{1-6}$ alkyl, $C_{3-7}$ cycloalkyl or $C_{3-7}$ cycloalkyl-$C_{1-3}$ alkylene group.

In the context of the invention the compounds of general formula (I) may therefore comprise two or more groups A identical to or different from one another.

Among the compounds of general formula (I) a first preferred subgroup of compounds is composed of the compounds for which:
m represents an integer from 1 to 4;
n represents an integer 1 or 2;
o an integer 1 or 2;
A is selected from one or more groups X and/or Y;
  X represents a methylene group optionally substituted by one or two $C_{1-6}$ alkyl groups, more particularly methyl;
  Y represents a $C_2$ alkynylene group;
B represents a covalent bond or a $C_{1-6}$ alkylene group, more particularly a methylene or an ethylene;
G represents a covalent bond or an oxygen atom;
$R_1$ represents a group $R_4$ optionally substituted by one or more groups $R_5$ and/or $R_6$, more particularly by one or two groups $R_5$ and/or $R_6$;
  $R_4$ represents a group selected from an oxazolyl, isoxazolyl, thiazolyl, phenyl, pyridinyl, naphthalenyl, quinolinyl, isoquinolinyl;
  $R_5$ represents a halogen atom, more particularly a chlorine, a bromine or a fluorine, a cyano group, a group $NR_7R_8$, or a $C_{1-6}$ alkyl group, more particularly a methyl or an isopropyl, a $C_{1-6}$ alkoxy group, more particularly a methoxy or an ethoxy, a $C_{1-6}$ fluoroalkyl group, more particularly a trifluoromethyl, or a $C_{1-6}$ fluoroalkoxy group, more particularly a trifluoromethoxy;
  $R_6$ represents a phenyl, phenyloxy or pyrimidinyloxy group; it being possible for the group or groups $R_6$ to be substituted by one or more groups $R_5$ identical to or different from one another;
  $R_7$ and $R_8$ represent independently of one another a $C_{1-6}$ alkyl group, more particularly a methyl;
$R_2$ represents a hydrogen atom or a $C_{1-6}$ alkyl group;
$R_3$ represents a hydrogen atom or a $C_{1-6}$ alkyl, $C_{3-7}$ cycloalkyl or $C_{3-7}$ cycloalkyl-$C_{1-3}$ alkylene group.

Among the compounds of general formula (I) and of the first subgroup, a second preferred subgroup is comprised of the compounds for which:

n, o, A, B, G, $R_1$, $R_2$ and $R_3$ are as defined in the formula (I) or in the subgroup above;

m represents an integer 1 or 2, more particularly 1.

Among the compounds of general formula (I) and of the subgroups above, a third preferred subgroup of compounds is composed of the compounds for which:
m, A, B, G, $R_1$, $R_2$ and $R_3$ are as defined in the formula (I) or in the subgroups above;
n is 2;
o is 2.

Among the compounds of general formula (I) and of the subgroups above, a fourth preferred subgroup is comprised of the compounds for which:
m, n, o, A, B, G, $R_2$ and $R_3$ are as defined in the formula (I) or in the subgroups above;
$R_1$ represents a group $R_4$ optionally substituted by one or more groups $R_5$ and/or $R_6$, more particularly by one or two groups $R_5$ and/or $R_6$;
  $R_4$ represents a group selected from an oxazolyl, isoxazolyl, phenyl or naphthalenyl;
  $R_5$ represents a halogen atom, more particularly a chlorine, a bromine or a fluorine, a cyano group, a group $NR_7R_8$, a $C_{1-6}$ alkyl group, more particularly a methyl or an isopropyl, a $C_{1-6}$ alkoxy group, more particularly a methoxy or an ethoxy, a $C_{1-6}$ fluoroalkyl group, more particularly a trifluoromethyl, or a $C_{1-6}$ fluoroalkoxy group, more particularly a trifluoromethoxy;

$R_6$ represents a phenyl, phenyloxy or pyrimidinyloxy group; it being possible for the group or groups $R_6$ to be substituted by one or more groups $R_5$ identical to or different from one another;

$R_7$ and $R_8$ represent independently of one another a $C_{1-6}$ alkyl group, more particularly a methyl.

Among the compounds of general formula (I) a fifth preferred subgroup is comprised of the compounds for which:
m, n, o, A, B, G, and $R_1$ are as defined in the formula (I) or in the subgroups above;

$R_2$ represents a hydrogen atom;

$R_3$ represents a hydrogen atom or a $C_{1-6}$ alkyl group, more particularly a methyl.

Among the compounds of general formula (I) mention may be made of the following compounds:

2-(methylamino)-2-oxoethyl{1-[(3,4'-difluorobiphenyl-4-yl)methyl]piperidin-4-yl}methylcarbamate;
2-(methylamino)-2-oxoethyl{1-[(3-chloro-4'-fluorobiphenyl-4-yl)methyl]piperidin-4-yl}methylcarbamate;
2-(methylamino)-2-oxoethyl{1-[3-(4-fluorophenoxy)benzyl]piperidin-4-yl}methylcarbamate;
2-(methylamino)-2-oxoethyl{1-[4-(4-chloro-3-fluorophenoxy)benzyl]piperidin-4-yl}methylcarbamate;
2-(methylamino)-2-oxoethyl 2-{1-[3-(trifluoromethoxy)benzyl]piperidin-4-yl}ethylcarbamate;
2-(methylamino)-2-oxoethyl 2-{1-[4-(trifluoromethoxy)benzyl]piperidin-4-yl}ethylcarbamate;
2-(methylamino)-2-oxoethyl 2-[1-(3-tert-butoxybenzyl)piperidin-4-yl]ethylcarbamate;
2-(methylamino)-2-oxoethyl 2-[1-(3-tert-butoxybenzyl)piperidin-4-yl]methylcarbamate;
2-(methylamino)-2-oxoethyl 2-[1-(2,4-dichlorobenzyl)piperidin-4-yl]ethylcarbamate;
2-(methylamino)-2-oxoethyl 2-[1-(2,5-dichlorobenzyl)piperidin-4-yl]ethylcarbamate;
2-(methylamino)-2-oxoethyl 2-[1-(3,5-dichlorobenzyl)piperidin-4-yl]ethylcarbamate;
2-(methylamino)-2-oxoethyl 2-[1-(2-chloro-5-fluorobenzyl)piperidin-4-yl]ethylcarbamate;
2-(methylamino)-2-oxoethyl 2-[1-(3-chloro-2-fluorobenzyl)piperidin-4-yl]ethylcarbamate;
2-(methylamino)-2-oxoethyl 2-[1-(3-chloro-5-methylbenzyl)piperidin-4-yl]ethylcarbamate;
2-(methylamino)-2-oxoethyl 2-{1-[(3,4'-difluorobiphenyl-4-yl)methyl]piperidin-4-yl}ethylcarbamate;
2-(methylamino)-2-oxoethyl 2-{1-[(3-chloro-4'-fluorobiphenyl-4-yl)methyl]piperidin-4-yl}ethylcarbamate;
2-(methylamino)-2-oxoethyl 2-{1-[4-(4-chloro-3-fluorophenoxy)benzyl]piperidin-4-yl}ethylcarbamate;
2-(methylamino)-2-oxoethyl{1-[3-(4-fluorophenoxy)benzyl]piperidin-4-yl}carbamate;
2-(methylamino)-2-oxoethyl{1-[3-(trifluoromethoxy)benzyl]piperidin-4-yl}methylcarbamate;
2-(methylamino)-2-oxoethyl{1-[4-(trifluoromethoxy)benzyl]piperidin-4-yl}methylcarbamate;
2-(methylamino)-2-oxoethyl{1-[3-(pyrimidin-2-yloxy)benzyl]piperidin-4-yl}methylcarbamate;
2-(methylamino)-2-oxoethyl 2-[1-(2-chloro-4-fluorobenzyl)piperidin-4-yl]ethylcarbamate;
2-(methylamino)-2-oxoethyl 2-[1-(3-chloro-4-fluorobenzyl)piperidin-4-yl]ethylcarbamate;
2-(methylamino)-2-oxoethyl 2-[1-(3-cyano-5-fluorobenzyl)piperidin-4-yl]ethylcarbamate;
2-(methylamino)-2-oxoethyl 2-{1-[3-(4-fluorophenoxy)benzyl]piperidin-4-yl}ethylcarbamate;
2-(methylamino)-2-oxoethyl(1-{[3-(4-chlorophenyl)isoxazol-5-yl]methyl}piperidin-4-yl)methylcarbamate;
2-(methylamino)-2-oxoethyl(1-{[5-(4-chlorophenyl)-1,3-oxazol-2-yl]methyl}piperidin-4-yl)methylcarbamate;
2-(methylamino)-2-oxoethyl[1-({4-[4-(trifluoromethyl)phenyl]-1,3-thiazol-2-yl}methyl)piperidin-4-yl]methylcarbamate;
2-(methylamino)-2-oxoethyl 2-(1-{[3-(4-chlorophenyl)isoxazol-5-yl]methyl}piperidin-4-yl)ethylcarbamate;
2-(methylamino)-2-oxoethyl 2-(1-{[5-(4-chlorophenyl)-1,3-oxazol-2-yl]methyl}piperidin-4-yl)ethylcarbamate;
2-(methylamino)-2-oxoethyl 2-[1-({4-[4-(trifluoromethyl)phenyl]-1,3-thiazol-2-yl}methyl)piperidin-4-yl]ethylcarbamate;
2-(methylamino)-2-oxoethyl(1-{2-[5-(4-chlorophenyl)isoxazol-3-yl]ethyl}piperidin-4-yl)methylcarbamate;
2-(methylamino)-2-oxoethyl 2-(1-{2-[3-(4-chlorophenyl)isoxazol-5-yl]ethyl}piperidin-4-yl)ethylcarbamate;
2-(methylamino)-2-oxoethyl(1-{2-[3-(4-chlorophenyl)isoxazol-5-yl]ethyl}piperidin-4-yl)methylcarbamate;
2-(methylamino)-2-oxoethyl(1-{3-[3-(4-chlorophenyl)isoxazol-5-yl]propyl}piperidin-4-yl)methylcarbamate;
2-(methylamino)-2-oxoethyl(1-{3-[5-(4-chlorophenyl)isoxazol-3-yl]propyl}piperidin-4-yl)methylcarbamate;
2-(methylamino)-2-oxoethyl{1-[1-(2-chloro-4-fluorophenyl)ethyl]piperidin-4-yl}methylcarbamate;
2-(methylamino)-2-oxoethyl(1-{1-[3-(4-chlorophenoxy)phenyl]ethyl}piperidin-4-yl)methylcarbamate;
2-(methylamino)-2-oxoethyl(1-{1-[2-chloro-3-(4-chlorophenoxy)phenyl]ethyl}piperidin-4-yl)methylcarbamate;
2-(methylamino)-2-oxoethyl 2-(1-{1-[3-(trifluoromethoxy)phenyl]ethyl}piperidin-4-yl)ethylcarbamate;
2-(methylamino)-2-oxoethyl 2-{1-[1-(2-chloro-4-fluorophenyl)ethyl]piperidin-4-yl}ethylcarbamate;
2-(methylamino)-2-oxoethyl{1-[4-(4-chlorophenyl)but-3-yn-1-yl]piperidin-4-yl}carbamate;
2-(methylamino)-2-oxoethyl{1-[5-(4-chlorophenyl)pent-4-yn-1-yl]piperidin-4-yl}carbamate;
2-(methylamino)-2-oxoethyl{1-[5-(2,5-dichlorophenyl)pent-4-yn-1-yl]piperidin-4-yl}carbamate;
2-(methylamino)-2-oxoethyl{1-[4-(4-chlorophenyl)but-3-yn-1-yl]piperidin-4-yl}methylcarbamate;
2-(methylamino)-2-oxoethyl{1-[4-(4-chloro-2-fluorophenyl)but-3-yn-1-yl]piperidin-4-yl}methylcarbamate;
2-(methylamino)-2-oxoethyl{1-[4-(2,5-dichlorophenyl)but-3-yn-1-yl]piperidin-4-yl}methylcarbamate.

Among the compounds of general formula (I) a preferred subclass of the group is comprised of compounds of the general formula (I'):

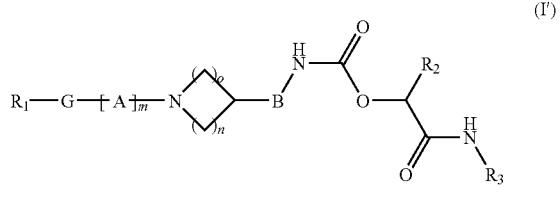

in which
m represents an integer from 1 to 4;
n represents an integer 1, 2 or 3;
o an integer 1 or 2;
A is selected from one or more groups X, Y and/or Z;

X represents a methylene group optionally substituted by one or two $C_{1-6}$ alkyl, $C_{3-7}$ cycloalkyl or $C_{3-7}$ cycloalkyl-$C_{1-3}$ alkylene groups;

Y represents either a $C_2$ alkenylene group optionally substituted by one or two $C_{1-6}$ alkyl, $C_{3-7}$ cycloalkyl or $C_{3-7}$ cycloalkyl-$C_{1-3}$ alkylene groups, or a $C_2$ alkynylene group;

Z represents a group of formula:

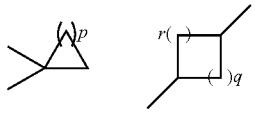

p represents an integer from 1 to 5;

q and r represent integers and are defined such that r+q is a number from 1 to 5;

B represents a covalent bond or a $C_{1-6}$ alkylene group;

G represents a covalent bond, an oxygen or sulphur atom or a —CH(OH)—, CO, SO or $SO_2$ group;

$R_1$ represents a group $R_4$ optionally substituted by one or more groups $R_5$ and/or $R_6$;

$R_4$ represents a group selected from a furanyl, pyrrolyl, thienyl, oxazolyl, isoxazolyl, thiazolyl, isothiazolyl, imidazolyl, pyrazolyl, thiadiazolyl, isothiadiazolyl, oxadiazolyl, thiadiazolyl, triazolyl, tetrazolyl, phenyl, pyridinyl, pyridazinyl, pyrimidinyl, pyrazinyl, triazinyl, naphthalenyl, quinolinyl, tetrahydroquinolinyl, isoquinolinyl, tetrahydroisoquinolinyl, phthalazinyl, quinazolinyl, quinoxalinyl, cinnolinyl, naphthyridinyl, imidazopyrimidinyl, thienopyrimidinyl, benzofuranyl, dihydrobenzofuranyl, benzothienyl, dihydrobenzothienyl, benzimidazolyl, benzoxazolyl, benzisoxazolyl, benzothiazolyl, benzisothiazolyl, indolyl, isoindolyl, indazolyl, pyrrolopyridinyl, furopyridinyl, dihydrofuropyridinyl, thienopyridinyl, dihydrothienopyridinyl, imidazopyridinyl, pyrazolopyridinyl, oxazolopyridinyl, isoxazolopyridinyl, thiazolopyridinyl;

$R_5$ represents a halogen atom, a cyano, nitro, hydroxyl, $C_{1-6}$ alkyl, $C_{1-6}$ alkoxy, $C_{1-6}$ thioalkyl, $C_{1-6}$ fluoroalkyl, $C_{1-6}$ fluoroalkoxy, $C_{1-6}$ fluorothioalkyl, $C_{3-7}$ cycloalkyl or $C_{3-7}$ cycloalkyl-$C_{1-3}$ alkylene group or a group $NR_7R_8$, $NR_7COR_8$, $NR_7CO_2R_8$, $NR_7SO_2R_8$, $COR_7$, $CO_2R_7$, $CONR_7R_8$, $SO_2R_7$, $SO_2NR_7R_8$ or —O—($C_{1-3}$ alkylene)-O—;

$R_6$ represents a phenyl, phenyloxy, benzyloxy, pyridinyl, pyrazinyl, pyridazinyl or pyrimidinyl group; it being possible for the group or groups $R_6$ to be substituted by one or more groups $R_5$ identical to or different from one another;

$R_7$ and $R_8$ represent independently of one another a hydrogen atom or a $C_{1-6}$ alkyl group, or, with the atom or atoms which carry them, form a ring selected from an azetidine, pyrrolidine, piperidine, morpholine, thiomorpholine, azepine or piperazine ring, this ring being optionally substituted by a $C_{1-6}$ alkyl or benzyl group;

$R_2$ represents a hydrogen atom or a $C_{1-6}$ alkyl group;

$R_3$ represents a hydrogen atom or a $C_{1-6}$ alkyl, $C_{3-7}$ cycloalkyl or $C_{3-7}$ cycloalkyl-$C_{1-3}$ alkylene group.

Among the compounds of general formula (I') a more preferred subgroup is composed of the compounds for which:

m represents an integer from 1 to 3;

n represents an integer 1 or 2;

o an integer 2;

A is a methylene group;

B represents a covalent bond or a $C_{1-6}$ alkylene group, more particularly a methylene or an ethylene;

G represents a covalent bond or an oxygen atom;

$R_1$ represents a group $R_4$ optionally substituted by one or more groups $R_5$ and/or $R_6$, more particularly by one or two groups $R_5$ and/or $R_6$;

$R_4$ represents a group selected from a phenyl, pyridinyl, naphthalenyl, isoquinolinyl;

$R_5$ represents a halogen atom, more particularly a chlorine, a bromine or a fluorine, a cyano group, an N,N-dimethylamino group, a $C_{1-6}$ alkyl group, more particularly an isopropyl, a $C_{1-6}$ alkoxy group, more particularly a methoxy or an ethoxy, or a $C_{1-6}$ fluoroalkyl group, more particularly a trifluoromethyl;

$R_6$ represents a phenyl group;

$R_2$ represents a hydrogen atom or a $C_{1-6}$ alkyl group;

$R_3$ represents a hydrogen atom or a $C_{1-6}$ alkyl, $C_{3-7}$ cycloalkyl or $C_{3-7}$ cycloalkyl-$C_{1-3}$ alkylene group.

Among the compounds of general formula (I') a second subgroup of compounds is composed of the compounds for which:

m, n, o, A, B, G and $R_1$ are as defined in subgroup 1;

$R_2$ represents hydrogen atom;

$R_3$ represents a hydrogen atom or a $C_{1-6}$ alkyl group, more particularly a methyl.

Among the compounds of general formula (I') specifically, the more preferred group of compounds consist of the following:

2-(methylamino)-2-oxoethyl{1-[(2-chlorophenyl)methyl]piperidin-4-yl}methylcarbamate;

2-(methylamino)-2-oxoethyl{1-[(4-chlorophenyl)methyl]piperidin-4-yl}methylcarbamate;

2-(methylamino)-2-oxoethyl{1-[(4-chlorophenyl)methyl]piperidin-4-yl}carbamate;

2-(methylamino)-2-oxoethyl(1-[4-(1-methylethyl)phenyl]methyl piperidin-4-yl)methylcarbamate;

2-(methylamino)-2-oxoethyl[1-(biphenyl-4-ylmethyl)piperidin-4-yl]carbamate;

2-(methylamino)-2-oxoethyl[1-(biphenyl-4-ylmethyl)piperidin-4-yl]methylcarbamate;

2-(methylamino)-2-oxoethyl 2-[1-(biphenyl-4-ylmethyl)piperidin-4-yl]ethylcarbamate;

2-(methylamino)-2-oxoethyl[1-(2-biphenyl-4-ylethyl)piperidin-4-yl]carbamate;

2-(methylamino)-2-oxoethyl[1-(naphthalen-2-ylmethyl)piperidin-4-yl]methylcarbamate;

2-(methylamino)-2-oxoethyl 2-{1-[(4-bromophenyl)methyl]piperidin-4-yl}ethylcarbamate;

2-(methylamino)-2-oxoethyl 2-(1-{[3-(trifluoromethyl)phenyl]methyl}piperidin-4-yl)ethylcarbamate;

2-(methylamino)-2-oxoethyl 2-(1-{[4-(trifluoromethyl)phenyl]methyl}piperidin-4-yl)ethylcarbamate;

2-(methylamino)-2-oxoethyl 2-{1-[(2,3-dichlorophenyl)methyl]piperidin-4-yl}ethylcarbamate;

2-(methylamino)-2-oxoethyl 2-{1-[(3,4-dichlorophenyl)methyl]piperidin-4-yl}ethylcarbamate;

2-(methylamino)-2-oxoethyl 2-[1-(naphthalen-1-ylmethyl)piperidin-4-yl]ethylcarbamate;

2-(methylamino)-2-oxoethyl 2-[1-(naphthalen-2-ylmethyl)piperidin-4-yl]ethylcarbamate;

2-(methylamino)-2-oxoethyl 2-[1-(pyridin-2-ylmethyl)piperidin-4-yl]ethylcarbamate;

2-(methylamino)-2-oxoethyl(1-{2-[4-fluoro-2-(methyloxy)phenyl]ethyl}piperidin-4-yl)methylcarbamate;

2-(methylamino)-2-oxoethyl(1-{2-[(4-fluorophenyl)oxy]ethyl}piperidin-4-yl)carbamate;

2-(methylamino)-2-oxoethyl(1-{2-[(4-chlorophenyl)oxy]ethyl}piperidin-4-yl)carbamate;
2-(methylamino)-2-oxoethyl(1-{2-[(2,4-dichlorophenyl)oxy]ethyl}piperidin-4-yl)carbamate;
2-(methylamino)-2-oxoethyl(1-{2-[(4-chlorophenyl)oxy]ethyl}piperidin-4-yl)methylcarbamate;
2-(methylamino)-2-oxoethyl 1-{2-[(2,4-dichlorophenyl)oxy]ethyl}piperidin-4-yl)methylcarbamate;
2-(methylamino)-2-oxoethyl 2-(1-{2-[(4-fluorophenyl)oxy]ethyl}piperidin-4-yl)ethylcarbamate;
2-(methylamino)-2-oxoethyl 2-(1-{2-[(4-chlorophenyl)oxy]ethyl}piperidin-4-yl)ethylcarbamate;
2-(methylamino)-2-oxoethyl(1-{2-[(4-fluorophenyl)oxy]ethyl}pyrrolidin-3-yl)methylcarbamate;
2-(methylamino)-2-oxoethyl(1-{2-[(4-chlorophenyl)oxy]ethyl}pyrrolidin-3-yl)methylcarbamate;
2-(methylamino)-2-oxoethyl(1-{2-[3-(trifluoromethyl)phenyl]ethyl}piperidin-4-yl)carbamate;
2-(methylamino)-2-oxoethyl{1-[2-(4-chlorophenyl)ethyl]piperidin-4-yl}carbamate;
2-(methylamino)-2-oxoethyl{1-[2-(4-cyanophenyl)ethyl]piperidin-4-yl}carbamate;
2-(methylamino)-2-oxoethyl(1-{2-[(isoquinolin-5-yl)oxy]ethyl}piperidin-4-yl)carbamate;
2-(methylamino)-2-oxoethyl[1-(2-naphthalen-1-ylethyl)piperidin-4-yl]carbamate;
2-(methylamino)-2-oxoethyl[1-(2-naphthalen-2-ylethyl)piperidin-4-yl]carbamate;
2-(methylamino)-2-oxoethyl{1-[3-(4-chlorophenyl)propyl]piperidin-4-yl}carbamate;
2-(methylamino)-2-oxoethyl(1-{3-[4-(methyloxy)phenyl]propyl}piperidin-4-yl)carbamate;
2-(methylamino)-2-oxoethyl{1-[2-(3-chlorophenyl)ethyl]piperidin-4-yl}methylcarbamate;
2-(methylamino)-2-oxoethyl(1-{2-[4-(ethyloxy)phenyl]ethyl}piperidin-4-yl)methylcarbamate;
2-(methylamino)-2-oxoethyl(1-{2-[4-(dimethylamino)phenyl]ethyl}piperidin-4-yl)methylcarbamate;
2-(methylamino)-2-oxoethyl{1-[2-(2,4-dichlorophenyl)ethyl]piperidin-4-yl}methylcarbamate;
2-(methylamino)-2-oxoethyl[1-(2-naphthalen-1-ylethyl)piperidin-4-yl]methylcarbamate;
2-(methylamino)-2-oxoethyl[1-(2-naphthalen-2-ylethyl)piperidin-4-yl]methylcarbamate;
2-(methylamino)-2-oxoethyl(1-{3-[4-(methyloxy)phenyl]propyl}piperidin-4-yl)methylcarbamate;
2-(methylamino)-2-oxoethyl 2-{1-[2-(2-chlorophenyl)ethyl]piperidin-4-yl}ethylcarbamate;
2-(methylamino)-2-oxoethyl 2-{1-[2-(4-fluorophenyl)ethyl]piperidin-4-yl}ethylcarbamate;
2-(methylamino)-2-oxoethyl 2-(1-{2-[4-(ethyloxy)phenyl]ethyl}piperidin-4-yl)ethylcarbamate;
2-(methylamino)-2-oxoethyl 2-{1-[2-(2-chloro-6-fluorophenyl)ethyl]piperidin-4-yl}ethylcarbamate;
2-(methylamino)-2-oxoethyl 2-(1-{3-[4-(methyloxy)phenyl]propyl}piperidin-4-yl)ethylcarbamate.

The compounds of general formula (I) may include one or more asymmetric carbons. They may exist in the form of enantiomers or diastereoisomers. These enantiomers and diastereoisomers, and also mixtures thereof, including the racemic mixtures, are also species of the present invention.

The compounds of formula (I) may exist in the form of bases or of addition salts with acids. Such addition salts are claimed species as well.

These salts are advantageously prepared with pharmaceutically acceptable acids, although the salts of other acids which are of use, for example, for purifying or isolating compounds of formula (I) likewise fall within the scope of the present invention.

The compounds of general formula (I) may be in the form of hydrates or solvates, namely in the form of associations or combinations with one or more molecules of water or with a solvent. Such hydrates and solvates likewise fall within the scope of the present invention.

In the context of the present application, the following terms used are to be construed as follows are understood as follows:

$C_{t-z}$, where t and z may take the values from 1 to 7, is a carbon chain which may have from t to z carbon atoms; for example, $C_{1-3}$ is a carbon chain which may have from 1 to 3 carbon atoms;

alkyl is a saturated, linear or branched aliphatic group; for example, a $C_{1-6}$ alkyl group represents a linear or branched carbon chain of 1 to 6 carbon atoms, more particularly a methyl, ethyl, propyl, isopropyl, butyl, isobutyl, tert-butyl, pentyl or hexyl;

alkylene is a saturated, linear or branched divalent alkyl group; for example, a $C_{1-3}$ alkylene group represents a linear or branched, divalent carbon chain of 1 to 3 carbon atoms, more particularly a methylene, ethylene, 1-methyl-ethylene or propylene;

cycloalkyl is a cyclic alkyl group; for example, a $C_{3-7}$ cycloalkyl group represents a cyclic carbon group of 3 to 7 carbon atoms, more particularly a cyclopropyl, cyclobutyl, cyclopentyl, cyclohexyl or cycloheptyl;

alkenylene is a divalent unsaturated aliphatic group having 2 carbons, more particularly an ethylene;

$C_2$ alkynylene is a —C≡C— group;

alkoxy is an —O-alkyl group having a saturated, linear or branched aliphatic chain;

thioalkyl is an —S-alkyl group having a saturated, linear or branched aliphatic chain;

fluoroalkyl is an alkyl group of which one or more hydrogen atoms have been substituted by a fluorine atom;

fluoroalkoxy is an alkoxy group of which one or more hydrogen atoms have been substituted by a fluorine atom;

fluorothioalkyl is a thioalkyl group of which one or more hydrogen atoms have been substituted by a fluorine atom; and halogen atom is a fluorine, a chlorine, a bromine or an iodine.

In the text below, a protective group Pg is understood to be a group which makes it possible on the one hand for a reactive function such as a hydroxyl or an amine to be protected during a synthesis and on the other hand for the reactive function to be regenerated intact at the end of synthesis. Examples of protective groups and also of methods of protection and deprotection are given in "Protective Groups in Organic Synthesis", Green et al., 2nd Edition (John Wiley & Sons, Inc., New York).

The compounds of the invention may be prepared according to various methods, which are illustrated by scheme 1 below.

Thus a first method (scheme 1) involves reacting a compound of general formula (II), in which B, $R_2$, n and o are as defined in the general formula (I), with a derivative of general formula (III), in which W represents a mesylate or tosylate group or a chlorine, bromine or iodine atom and m, G, A and $R_1$ are as defined in the general formula (I), in the presence of a base such as triethylamine, sodium hydride, sodium tert-butoxide or sodium carbonate in a solvent such as tetrahydrofuran, acetonitrile, dimethyl sulphoxide or dimethylformamide at a temperature between 0° C. and the reflux temperature of the solvent.

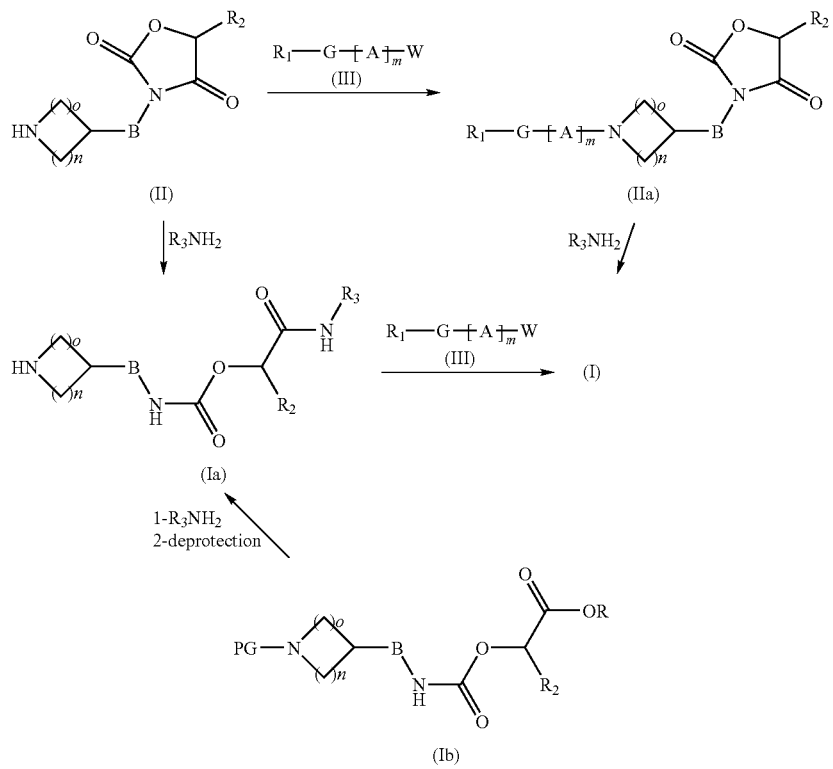

Scheme 1

The oxazolidine-dione of general formula (IIa) thus obtained is subsequently converted into a compound of general formula (I), by aminolysis using an amine of general formula $R_3NH_2$ in which $R_3$ is as defined in the general formula (I). The aminolysis reaction may be carried out in a solvent such as methanol, ethanol or a solvent mixture such as methanol and tetrahydrofuran or methanol and dioxane.

A variant form of obtaining compounds of general formula (I) (scheme 1) involves converting a compound of general formula (II) as defined above by aminolysis, under the conditions described above, using an amine of general formula $R_3NH_2$ as defined above, to give a carbamate-amide derivative of general formula (Ia) in which B, $R_2$, $R_3$, n and o are as defined in the general formula (I). The compound of general formula (I) is then obtained by reacting the compound (Ia) with a derivative of general formula (III) as defined above, under the conditions described above.

The carbamate-amide derivative of general formula (Ia) as defined above may also be obtained from the carbamate-ester of general formula (Ib), in which B, $R_2$, n and o are as defined in the general formula (I), PG represents a protective group such as a Boc(tert-butyloxycarbonyl) and R represents a methyl or ethyl group, by aminolysis using an amine of general formula $R_3NH_2$ as defined above and under the conditions described above, then by deprotection, in the presence for example of a solution of hydrochloric acid (5N) in isopropanol.

The carbamate-esters (Ib) may be prepared according to the method illustrated by scheme 2 below.

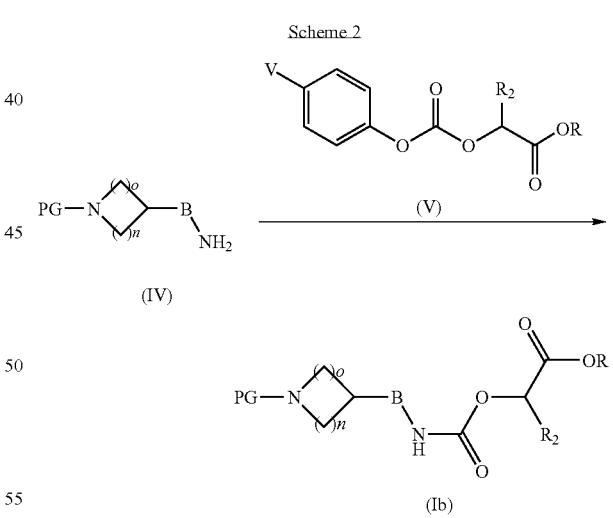

Scheme 2

According to scheme 2 the carbamate-ester of general formula (Ib) is obtained by reacting an amine of general formula (IV), in which B, n and o are as defined in the general formula (I) and PG represents a protective group such as a Boc, with a carbonate of general formula (V), in which V represents a hydrogen atom or a nitro group, $R_2$ is as defined in the general formula (I) and R represents a methyl or ethyl group.

When the method of preparing them is not described the compounds of general formula (II) may be prepared according to methods which are described in the literature or according to methods similar to those described or known to the skilled person.

The carbonates of general formula (V) may be prepared according to any method described in the literature, by reaction for example of an alcohol of general formula HOCHR$_2$COOR where R represents a methyl or ethyl group with phenyl chloroformate or 4-nitrophenyl chloroformate in the presence of a base such as triethylamine or diisopropylethylamine.

The compounds of general formulae (III) and (IV) and the amines of general formula R$_3$NH$_2$ are available commercially or are prepared according to methods which are described in the literature or which are known to the skilled person.

The compounds of general formula (Ia) in which B, R$_2$, R$_3$, n and o are as defined in the general formula (I) are novel and likewise form part of the invention. They are useful as synthesis intermediates for the preparation of compounds of general formula (I).

The compounds of general formula (IIa) in which m, G, A, R$_1$, B, R$_2$, n and o are as defined in the general formula (I), with the excluding the compound 3-[1-(phenylmethyl)-4-piperidinyl]-2,4-oxazolidinedione, are novel and likewise form part of the invention. They are useful as synthesis intermediates for preparing compounds of general formula (I).

The following examples are provided to better describe and delineate the methods of preparation of but some of the compounds of the present invention. These examples are for illustrative purposes only, and should not be construed as limiting the spirit and scope of the invention as defined by the claims that follow. The microanalyses, the IR and NMR spectra and/or the LC-MS (liquid chromatography coupled to mass spectroscopy) confirm the structures and the purities of the compounds obtained.

M.P. (° C.) represents the melting point in degrees Celsius.

The numbers indicated between brackets in the titles of the examples correspond to those in the 1st column of the subsequent table.

EXAMPLE 1 (COMPOUND 25)

2-(methylamino)-2-oxoethyl 2-[1-(biphenyl-4-ylmethyl)piperidin-4-yl]ethylcarbamate

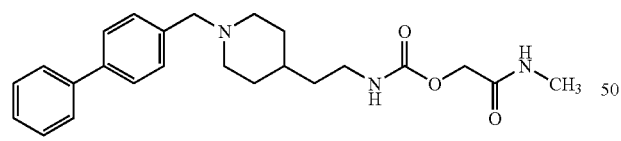

1.1. 3-(2-piperidin-4-ylethyl)-1,3-oxazolidine-2,4-dione hydrochloride

A solution of 10 g (77.40 mmol) of 2-piperidin-4-ylethanol, 22.33 g (85.14 mmol) of triphenylphosphine and 9.39 g (92.88 mmol) of 1,3-oxazolidine-2,4-dione (J. Med. Chem. 1991, 34, 1538-44) in 150 ml of tetrahydrofuran, cooled to approximately −10° C., is admixed dropwise under an inert atmosphere with a solution of 15.65 g (77.40 mmol) of diisopropyl azodicarboxylate (DIAD) in 25 ml of tetrahydrofuran, during which the temperature of the reaction mixture is held between −10° C. and 0° C. Stirring is continued at 0° C. for 1 hour and then at 25° C. for 22 hours. The solid formed is collected by filtration, washed repeatedly with tetrahydrofuran and then dried under vacuum at approximately 70° C. This solid is then taken up in a solution of hydrochloric acid (5N) in isopropanol. The solid formed is collected by filtration and then washed with ethyl acetate and ether.

Drying under vacuum at approximately 70° C. gives 6.45 g of hydrochloride in the form of a white solid.

M.P. (° C.): 178° C.

1.2. 3-{2-[1-(biphenyl-4-ylmethyl)piperidin-4-yl]ethyl}-1,3-oxazolidine-2,4-dione A solution of 0.40 g (1.61 mmol) of 3-(2-piperidin-4-ylethyl)-1,3-oxazolidine-2,4-dione hydrochloride, prepared in step 1.1., 0.326 g (1.61 mmol) of 4-(chloromethyl)biphenyl and 0.51 g (4.82 mmol) of sodium carbonate in 3 ml of acetonitrile is heated at reflux for 17 hours. It is left to return to ambient temperature and filtered and the filtrate is concentrated under reduced pressure. The residue is taken up in dichloromethane and water and the aqueous phase is separated off and extracted twice with dichloromethane. The combined organic phases are washed with saturated aqueous sodium chloride solution and dried over sodium sulphate. Following evaporation of the solvent, the residue obtained is purified by chromatography on silica gel, eluting with a 97/3 then 95/5 mixture of dichloromethane and methanol.

This gives 0.46 g of product in the form of a beige solid.

1.3. 2-(methylamino)-2-oxoethyl 2-[1-(biphenyl-4-ylmethyl)piperidin-4-yl]ethylcarbamate A solution of 0.45 g (1.19 mmol) of 3-{2-[1-(biphenyl-4-ylmethyl)piperidin-4-yl]ethyl}-1,3-oxazolidine-2,4-dione, obtained in step 1.2., in 5 ml of methanol is admixed with 3 ml (5.97 mmol) of a solution of methylamine (2M) in tetrahydrofuran. Stirring is continued at ambient temperature for 17 hours. Following concentration under reduced pressure, the residue obtained is purified by chromatography on silica gel, eluting with a 95/5 then 90/10 mixture of dichloromethane and methanol. A yellow paste is obtained which is crystallized from diisopropyl ether.

This gives 0.40 g of product in the form of a yellow solid.
LC-MS: M+H=410
M.P. (° C.): 106-110° C.
$^1$H NMR (CDCl$_3$) □ (ppm): 1.2-1.50 (unresolved complex, 5H); 1.70 (m, 2H); 2.0 (broad t, 2H); 2.90 (d, 3H); 3.0 (m, 2H); 3.30 (q, 2H); 3.55 (s, 2H); 4.60 (s, 2H); 4.80 (broad s, 1H); 6.15 (broad s, 1H); 7.40 (m, 5H); 7.60 (m, 4H).

EXAMPLE 2 (COMPOUND 52)

2-(methylamino)-2-oxoethyl 1-{2-[4-fluoro-2-(methoxy)-phenyl]ethyl}piperidin-4-yl)methylcarbamate

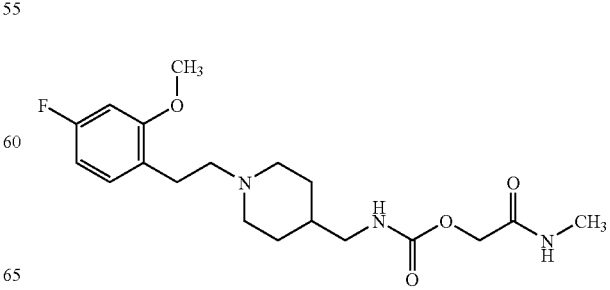

2.1. 1,1-dimethylethyl 4-{[(methylsulphonyl)-oxy]methyl}piperidine-1-carboxylate A solution of 10.08 g (46.81 mmol) of 1,1-dimethylethyl 4-(hydroxymethyl)piperidine-1-carboxylate and 9.90 ml (70.21 mmol) of triethylamine in 100 ml of dichloromethane, cooled to approximately 0° C., is admixed dropwise under an inert atmosphere with a solution of 4 ml (51.49 mmol) of mesyl chloride in 10 ml of dichloromethane. The bath is removed and stirring is continued at ambient temperature for 30 minutes. Water is added to the reaction mixture, the aqueous phase is separated off and extracted once with dichloromethane, the combined organic phases are washed with water and dried over sodium sulphate and the filtrate is concentrated under reduced pressure.

This gives 13.7 g of product in the form of an orange-coloured oil, which is used as it is in the following step.

2.2. 1,1-dimethylethyl 4-[(2,4-dioxo-1,3-oxazolidin-3-yl)methyl]piperidine-1-carboxylate A suspension of 13.60 g (46.36 mmol) of 1,1-dimethylethyl 4-{[(methylsulphonyl)oxy]methyl}piperidine-1-carboxylate, prepared in step 2.1., 9.37 g (92.72 mmol) of 1,3-oxazolidine-2,4-dione and 16.02 g (139.08 mmol) of 1,1,3,3-tetramethylguanidine in a mixture of 180 ml of tetrahydrofuran and 30 ml of dimethylformamide is heated at reflux for 24 hours. It is allowed to return to ambient temperature and is concentrated under reduced pressure. The residue is taken up in dichloromethane and water and the aqueous phase is separated off and extracted twice with dichloromethane. The combined organic phases are washed with saturated aqueous sodium chloride solution and dried over sodium sulphate. Following evaporation of the solvent, the residue obtained is purified by chromatography on silica gel, eluting with a 98/2 then 95/5 mixture of dichloromethane and methanol.

This gives 12.53 g of product in the form of an orange-brown solid.

2.3. 3-(piperidin-4-ylmethyl)-1,3-oxazolidine-2,4-dione hydrochloride

A suspension of 12.51 g (41.95 mmol) of 1,1-dimethylethyl 4-[(2,4-dioxo-1,3-oxazolidin-3-yl)methyl]piperidine-1-carboxylate, obtained in step 2.2., in 65 ml of dioxane is admixed with 38.10 ml (209.75 mmol) of a solution of hydrochloric acid (5N) in isopropanol. Stirring is continued at approximately 60° C. for 17 hours. The suspension is allowed to return to ambient temperature. The solid formed is collected by filtration and then washed repeatedly with ether and dried under vacuum at approximately 70° C.

This gives 8.41 g of product in the form of a white solid.
M.P. (° C.): 195-200° C.

2.4. 3-[(1-{2-[4-fluoro-2-(methoxy)phenyl]ethyl}piperidin-4-yl)methyl]-1,3-oxazolidine-2,4-dione The method described in Example 1 (step 1.2.) is used. Starting from 0.40 g (1.70 mmol) of 3-(piperidin-4-ylmethyl)-1,3-oxazolidine-2,4-dione hydrochloride prepared in step 2.3., 0.423 g (1.70 mmol) of 2-[4-fluoro-2-(methyloxy)phenyl]ethyl methanesulphonate [EP1340761] and 0.54 g (5.11 mmol) of sodium carbonate gives, after treatment, 0.590 g of product in the form of a viscous yellow oil, which is used as it is in the following step.

2.5. 2-(methylamino)-2-oxoethyl 1-{2-[4-fluoro-2-(methoxy)phenyl]ethyl]piperidin-4-yl)methylcarbamate The procedure described in Example 1 (step 1.3.) is followed. Starting from 0.58 g (1.66 mmol) of 3-[(1-{2-[4-fluoro-2-(methoxy)phenyl]ethyl}piperidin-4-yl)methyl]-1,3-oxazolidine-2,4-dione, prepared in step 2.4., and 8.28 ml (16.55 mmol) of a solution of methylamine (2M) in tetrahydrofuran, and after chromatography on silica gel, eluting with a 95/5/0.5 mixture of dichloromethane, methanol and 28% ammonia, followed by washing with diisopropyl ether, gives 0.315 g of product in the form of a white solid.

LC-MS: M+H=382

M.P. (° C.): 126-128° C.

$^1$H NMR (DMSO) □ (ppm): 1.10 (m, 2H); 1.35 (broad s, 1H); 1.60 (broad d, 2H); 1.85 (broad t, 2H); 2.40 (m, 2H); 2.60 (m, 5H); 2.90 (m, 4H); 3.80 (s, 3H); 4.30 (s, 2H); 6.65 (td, 1H); 6.80 (dd, 1H); 7.15 (m, 2H); 7.70 (broad s, 1H).

EXAMPLE 3 (COMPOUND 68)

2-(methylamino)-2-oxoethyl 1-{2-[(2,4-dichlorophenyl)oxy]ethyl}piperidin-4-yl)carbamate

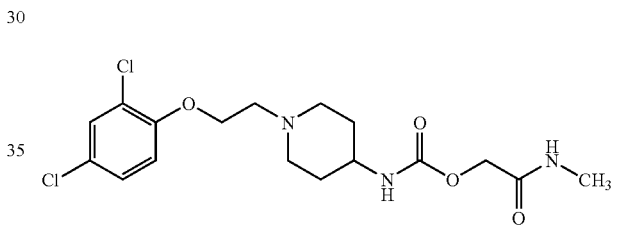

3.1. 1,1-dimethylethyl 4-[({[2-(ethyloxy)-2-oxoethyl]oxy}carbonyl)amino]piperidine-1-carboxylate A suspension of 5.09 g (25.42 mmol) of 1,1-dimethylethyl 4-aminopiperidine-1-carboxylate and 13.45 g (59.99 mmol) of ethyl [(phenyloxycarbonyl)oxy]acetate (J. Med. Chem., 1999, 42, 277-90) in 300 ml of toluene is heated at reflux for 30 hours.

The suspension is allowed to return to ambient temperature, the insoluble material is separated off by filtration and the filtrate is concentrated under reduced pressure. The residue thus obtained is purified by chromatography on silica gel, eluting with a 30/70 mixture of ethyl acetate and cyclohexane.

This gives 6.62 g of product in the form of a light-coloured yellow oil.

3.2. 1,1-dimethylethyl 4-[({[2-(methylamino)-2-oxoethyl]oxy}carbonyl)amino]piperidine-1-carboxylate The procedure of Example 1 (step 1.3.) is repeated. Starting from 6.33 g (19.16 mmol) of 1,1-dimethylethyl 4-[({[2-(ethyloxy)-2-oxoethyl]oxy}-carbonyl)amino]piperidine-1-carboxylate, prepared in step 3.1., and 47.90 ml (95.81 mmol) of a solution of methylamine (2M) in tetrahydrofuran gives 5.90 g of product in the form of a sticky yellow paste.

3.3. 2-(methylamino)-2-oxoethyl piperidin-4-ylcarbamate hydrochloride

The method described in Example 2 (step 2.3.) is used. Starting from 5.90 g (18.71 mmol) of 1,1-dimethylethyl 4-[({[2-methylamino)-2-oxoethyl]oxy}carbonyl)amino]piperidine-1-carboxylate, prepared in step 3.2., and 17 ml (93.53 mmol) of a solution of hydrochloric acid (5N) in isopropanol gives 3.83 g of hydrochloride in the form of a white solid after washing with diisopropyl ether and drying under vacuum at approximately 70° C.

M.P. (° C.): 153° C.

3.4. 2-(methylamino)-2-oxoethyl 1-{2-[2,4-dichlorophenyl)oxy]ethyl}piperidin-4-yl)carbamate The method described in Example 1 (step 1.2.) is used. Starting from 0.51 g (1.89 mmol) of 2-(methylamino)-2-oxoethyl piperidin-4-ylcarbamate hydrochloride, prepared in step 3.3., 0.50 g (1.99 mmol) of 1-[(2-bromoethyl)oxy]-2,4-dichlorobenzene and 0.60 g (5.68 mmol) of sodium carbonate, and after chromatography on silica gel, eluting with a 94/6/0.6 then 95/5/0.5 mixture of dichloromethane, methanol and 28% ammonia, followed by washing with diisopropyl ether, gives 0.44 g of product in the form of a white solid.

LC-MS: M+H=404

M.P. (° C.): 115-119° C.

$^1$H NMR (CDCl$_3$) □ (ppm): 1.50 (m, 2H); 2.0 (broad d, 2H); 2.35 (broad t, 2H); 2.90 (d, 3H); 3.0 (m, 4H); 3.60 (m, 1H); 4.15 (t, 2H); 4.60 (s, 2H); 4.75 (broad d, 1H); 6.15 (broad s, 1H); 6.85 (d, 1H); 7.20 (dd, 1H); 7.40 (d, 1H).

EXAMPLE 4 (COMPOUND 4)

2-(methylamino)-2-oxoethyl{1-[(4-chlorophenyl)methyl]piperidin-4-yl}methylcarbamate hydrochloride

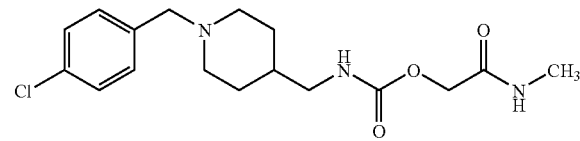

4.1. 2-(methylamino)-2-oxoethyl(piperidin-4-yl)methylcarbamate hydrochloride A solution of 0.50 g (2.13 mmol) of 3-piperidin-4-ylmethyl)-1,3-oxozolidine-2,4-dione hydrochloride, obtained in step 2.3., and 5.30 ml (10.65 mmol) of a solution of methylamine (2M) in tetrahydrofuran in 10 ml of methanol is stirred at ambient temperature for 15 hours. Following concentration under reduced pressure, the residue obtained is treated with a solution of hydrochloric acid (5N) in isopropanol. The hydrochloride obtained is collected by filtration, washed with diisopropyl ether and dried under vacuum at approximately 70° C. This gives 0.49 g of a white powder.

4.2. 2-(methylamino)-2-oxoethyl{1-[(4-chlorophenyl)methyl]piperidin-4-yl}methylcarbamate hydrochloride A mixture of 0.118 g (0.44 mmol) of 2-(methylamino)-2-oxoethyl (piperidin-4-yl)methylcarbamate hydrochloride, 0.283 g (1.33 mmol) of sodium triacetoxyborohydride and 0.626 g (4.45 mmol) of 4-chlorobenzaldehyde in 5 ml of a 1% solution of acetic acid in N,N'-dimethylformamide is stirred at ambient temperature. After 24 hours of stirring, 2 g of DOWEX 50WX2 acidic resin (Fluka) are added and stirring is continued at ambient temperature for one hour. The mixture is filtered and the resin is rinsed with 3 times 5 ml of N,N'-dimethylformamide, 3 times 5 ml of dichloromethane and 3 times 5 ml of methanol. The resin is subsequently treated for an hour at ambient temperature with 8 ml of a solution (2M) of ammonia in methanol. The mixture is filtered and the filtrate is concentrated under vacuum. The product is purified by chromatography on silica gel, eluting with a 94/6 mixture of dichloromethane and methanol containing 2% of 28% aqueous ammonia solution. The oily residue obtained is treated with 5 ml of a solution of hydrochloric acid (0.1N) in isopropanol. Concentration gives 0.067 g of a white powder.

M.P. (° C.): 220-222° C.

LC-MS: M+H=354

$^1$H NMR (DMSO-d$_6$/D$_2$O): □ (ppm): 1.20 (m, 2H); 1.40 (m, 1H); 1.60 (m, 2H); 1.90 (t, 2H); 2.70 (s, 3H); 2.75 (d, 2H); 2.90 (d, 2H); 3.40 (s, 2H); 4.30 (s, 2H); 7.95 (m, 4H).

Table 1 below illustrates the chemical structures and the physical properties of some compounds according to the invention.

In this table:
- in the "base or salt" column, "base" signifies that the compound is in the form of the free base, whereas "HCl" represents a compound in hydrochloride form, and the ratio between brackets is the (acid:base) ratio,
- t-BuO, Me, Et and i-Pr represent, respectively, tert-butoxy, methyl, ethyl and isopropyl groups, and
- Ph represents a phenyl group.

TABLE 1

(I)

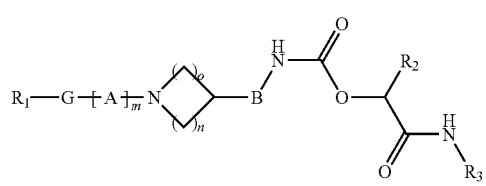

| Cpd | R$_1$ | G | [A]m | n | o | B | R$_2$ | R$_3$ | Base or salt | M.P. (° C.) |
|---|---|---|---|---|---|---|---|---|---|---|
| 1. | 4-Cl-phenyl | bond | CH$_2$ | 2 | 2 | bond | H | CH$_3$ | base | 144-146 |
| 2. | 4-Ph-phenyl | bond | CH$_2$ | 2 | 2 | bond | H | CH$_3$ | base | 165-167 |

TABLE 1-continued (I)

$R_1-G-[A]_m-N\underset{(\phantom{x})_n}{\overset{(\phantom{x})_o}{\bigg\langle}}B-\underset{H}{N}-\underset{\parallel}{C}-O-\underset{\underset{\parallel}{C}}{\overset{R_2}{C}H}-\underset{\parallel}{C}-\underset{H}{N}-R_3$

| Cpd | R$_1$ | G | [A]m | n | o | B | R$_2$ | R$_3$ | Base or salt | M.P. (° C.) |
|---|---|---|---|---|---|---|---|---|---|---|
| 3. | 2-Cl-phenyl | bond | CH$_2$ | 2 | 2 | CH$_2$ | H | CH$_3$ | HCl (1/1) | 173-175 |
| 4. | 4-Cl-phenyl | bond | CH$_2$ | 2 | 2 | CH$_2$ | H | CH$_3$ | HCl (1/1) | 220-222 |
| 5. | 4-iPr-phenyl | bond | CH$_2$ | 2 | 2 | CH$_2$ | H | CH$_3$ | HCl (1/1) | 159-161 |
| 6. | 4-Ph-phenyl | bond | CH$_2$ | 2 | 2 | CH$_2$ | H | CH$_3$ | HCl (1/1) | 205-207 |
| 7. | [2-F,4-(4-F-phenyl)]-phenyl | bond | CH$_2$ | 2 | 2 | CH$_2$ | H | CH$_3$ | base | 156-158 |
| 8. | [2-Cl,4-(4-F-phenyl)]-phenyl | bond | CH$_2$ | 2 | 2 | CH$_2$ | H | CH$_3$ | HCl (1/1) | 163-169 |
| 9. | 3-(4-F-phenyloxy)-phenyl | bond | CH$_2$ | 2 | 2 | CH$_2$ | H | CH$_3$ | HCl (1/1) | 163-165 |
| 10. | 4-[(3-F,4-Cl)-phenyl-oxy]phenyl | bond | CH$_2$ | 2 | 2 | CH$_2$ | H | CH$_3$ | base | 96-104 |
| 11. | naphthalen-2-yl | bond | CH$_2$ | 2 | 2 | eli 2 | H | CH$_3$ | HCl (1/1) | 156-157 |
| 12. | 4-Br-phenyl | bond | CH$_2$ | 2 | 2 | (CH$_2$)$_2$ | H | CH$_3$ | base | 107-111 |
| 13. | 3-CF$_3$-phenyl | bond | CH$_2$ | 2 | 2 | (CH$_2$)$_2$ | H | CH$_3$ | base | 90-92 |
| 14. | 4-CF$_3$-phenyl | bond | CH$_2$ | 2 | 2 | (CH$_2$)$_2$ | H | CH$_3$ | base | 116-120 |
| 15. | 3-CF$_3$O-phenyl | bond | CH$_2$ | 2 | 2 | (CH$_2$)$_2$ | H | CH$_3$ | base | 418* |
| 16. | 4-CF$_3$O-phenyl | bond | CH$_2$ | 2 | 2 | (CH$_2$)$_2$ | H | CH$_3$ | base | 109-111 |
| 17. | (2-Cl,3-Cl)-phenyl | bond | CH$_2$ | 2 | 2 | (CH$_2$)$_2$ | H | CH$_3$ | base | 114-116 |
| 18. | (2-Cl,4-Cl)-phenyl | bond | CH$_2$ | 2 | 2 | (CH$_2$)$_2$ | H | CH$_3$ | base | 117-119 |
| 19. | (2-Cl,5-Cl)-phenyl | bond | CH$_2$ | 2 | 2 | (CH$_2$)$_2$ | H | CH$_3$ | base | 125-127 |
| 20. | (3-Cl,4-Cl)-phenyl | bond | CH$_2$ | 2 | 2 | (CH$_2$)$_2$ | H | CH$_3$ | base | 101-105 |
| 21. | (3-Cl,5-Cl)-phenyl | bond | CH$_2$ | 2 | 2 | (CH$_2$)$_2$ | H | CH$_3$ | base | 124-126 |
| 22. | (2-Cl,5-F)-phenyl | bond | CH$_2$ | 2 | 2 | (CH$_2$)$_2$ | H | CH$_3$ | base | 102-104 |
| 23. | (2-F,3-Cl)-phenyl | bond | CH$_2$ | 2 | 2 | (CH$_2$)$_2$ | H | CH$_3$ | base | 104-106 |
| 24. | (3-Cl,5-CH$_3$)-phenyl | bond | CH$_2$ | 2 | 2 | (CH$_2$)$_2$ | H | CH$_3$ | base | 79-81 |
| 25. | 4-Ph-phenyl | bond | CH$_2$ | 2 | 2 | (CH$_2$)$_2$ | H | CH$_3$ | base | 106-110 |
| 26. | [2-F,4-(4-F-phenyl)]-phenyl | bond | CH$_2$ | 2 | 2 | (CH$_2$)$_2$ | H | CH$_3$ | base | 143-145 |
| 27. | [2-Cl,4-(4-F-phenyl)]-phenyl | bond | CH$_2$ | 2 | 2 | (CH$_2$)$_2$ | H | CH$_3$ | base | 98-102 |
| 28. | 4-[(3-F,4-Cl)-phenyl-oxy]phenyl | bond | CH$_2$ | 2 | 2 | (CH$_2$)$_2$ | H | CH$_3$ | base | 109-111 |
| 29. | naphthalen-1-yl | bond | CH$_2$ | 2 | 2 | (CH$_2$)$_2$ | H | CH$_3$ | base | 86-88 |
| 30. | naphthalen-2-yl | bond | CH$_2$ | 2 | 2 | (CH$_2$)$_2$ | H | CH$_3$ | base | 87-93 |
| 31. | pyridin-2-yl | bond | CH$_2$ | 2 | 2 | (CH$_2$)$_2$ | H | CH$_3$ | base | 104-106 |
| 32. | 3-CF$_3$-phenyl | bond | (CH$_2$)$_2$ | 2 | 2 | bond | H | CH$_3$ | HCl (1/1) | 136-138 |
| 33. | 4-Cl-phenyl | bond | (CH$_2$)$_2$ | 2 | 2 | bond | H | CH$_3$ | HCl (1/1) | 168-170 |

TABLE 1-continued (I)

$$R_1-G-[A]_m-N\underset{(CH_2)_n}{\overset{(CH_2)_o}{\diamond}}B-NH-C(=O)-O-CH(R_2)-C(=O)-NH-R_3$$

| Cpd | $R_1$ | G | $[A]_m$ | n | o | B | $R_2$ | $R_3$ | Base or salt | M.P. (° C.) |
|---|---|---|---|---|---|---|---|---|---|---|
| 34. | 4-CN-phenyl | bond | $(CH_2)_2$ | 2 | 2 | bond | H | $CH_3$ | base | 179-181 |
| 35. | (2-Cl,3-Cl)-phenyl | bond | $(CH_2)_2$ | 2 | 2 | bond | H | $CH_3$ | base | 117-123 |
| 36. | (2-Cl,4-Cl)-phenyl | bond | $(CH_2)_2$ | 2 | 2 | bond | H | $CH_3$ | base | 134-138 |
| 37. | (2-Cl,6-Cl)-phenyl | bond | $(CH_2)_2$ | 2 | 2 | bond | H | $CH_3$ | base | 163-167 |
| 38. | (3-Cl,4-Cl)-phenyl | bond | $(CH_2)_2$ | 2 | 2 | bond | H | $CH_3$ | base | 130-132 |
| 39. | 4-Ph-phenyl | bond | $(CH_2)_2$ | 2 | 2 | bond | H | $CH_3$ | base | 174-178 |
| 40. | 4-phenyloxy phenyl | bond | $(CH_2)_2$ | 2 | 2 | bond | H | $CH_3$ | base | 144-146 |
| 41. | naphthalen-1-yl | bond | $(CH_2)_2$ | 2 | 2 | bond | H | $CH_3$ | HCl (1/1) | 185-187 |
| 42. | 4-F-naphthalen-1-yl | bond | $(CH_2)_2$ | 2 | 2 | bond | H | $CH_3$ | base | 124-130 |
| 43. | naphthalen-2-yl | bond | $(CH_2)_2$ | 2 | 2 | bond | H | $CH_3$ | HCl (1/1) | 198-202 |
| 44. | 3-Cl-phenyl | bond | $(CH_2)_2$ | 2 | 2 | $CH_2$ | H | $CH_3$ | base | 93-95 |
| 45. | 4-EtO-phenyl | bond | $(CH_2)_2$ | 2 | 2 | $CH_2$ | H | $CH_3$ | base | 134-136 |
| 46. | 4-$Me_2$N-phenyl | bond | $(CH_2)_2$ | 2 | 2 | $CH_2$ | H | $CH_3$ | base | 130-132 |
| 47. | (2-Cl,3-Cl)-phenyl | bond | $(CH_2)_2$ | 2 | 2 | $CH_2$ | H | $CH_3$ | base | 81-87 |
| 48. | (2-Cl,4-Cl)-phenyl | bond | $(CH_2)_2$ | 2 | 2 | $CH_2$ | H | $CH_3$ | base | 125-127 |
| 49. | (2-Cl,4-Cl)-phenyl | bond | $(CH_2)_2$ | 2 | 2 | $CH_2$ | H | H | base | 115-119 |
| 50. | (2-Cl,6-Cl)-phenyl | bond | $(CH_2)_2$ | 2 | 2 | $CH_2$ | H | $CH_3$ | base | 144-148 |
| 51. | (3-Cl,4-Cl)-phenyl | bond | $(CH_2)_2$ | 2 | 2 | $CH_2$ | H | $CH_3$ | base | 123-127 |
| 52. | (2-MeO,4-F)-phenyl | bond | $(CH_2)_2$ | 2 | 2 | $CH_2$ | H | $CH_3$ | base | 126-128 |
| 53. | 4-phenyloxy phenyl | bond | $(CH_2)_2$ | 2 | 2 | $CH_2$ | H | $CH_3$ | base | 120-124 |
| 54. | naphthalen-1-yl | bond | $(CH_2)_2$ | 2 | 2 | $CH_2$ | H | $CH_3$ | HCl (1/1) | 148-150 |
| 55. | 4-F-naphthalen-1-yl | bond | $(CH_2)_2$ | 2 | 2 | $CH_2$ | H | $CH_3$ | base | 120-124 |
| 56. | naphthalen-2-yl | bond | $(CH_2)_2$ | 2 | 2 | $CH_2$ | H | $CH_3$ | base | 163-166 |
| 57. | 2-Cl-phenyl | bond | $(CH_2)_2$ | 2 | 2 | $(CH_2)_2$ | H | $CH_3$ | HCl (1/1) | 121-123 |
| 58. | 4-F-phenyl | bond | $(CH_2)_2$ | 2 | 2 | $(CH_2)_2$ | H | $CH_3$ | base | 122-124 |
| 59. | 4-EtO-phenyl | bond | $(CH_2)_2$ | 2 | 2 | $(CH_2)_2$ | H | $CH_3$ | base | 118-120 |
| 60. | (2-Cl,6-F)-phenyl | bond | $(CH_2)_2$ | 2 | 2 | $(CH_2)_2$ | H | $CH_3$ | base | 88-90 |
| 61. | 4-Cl-phenyl | bond | $(CH_2)_3$ | 2 | 2 | bond | H | $CH_3$ | HCl (1/1) | 132-134 |
| 62. | 4-MeO-phenyl | bond | $(CH_2)_3$ | 2 | 2 | bond | $CH_2$ | $CH_3$ | HCl (1/1) | 175-177 |
| 63. | 4-MeO-phenyl | bond | $(CH_2)_3$ | 2 | 2 | $CH_2$ | H | $CH_3$ | HCl (1/1) | 155-157 |
| 64. | 4-MeO-phenyl | bond | $(CH_2)_3$ | 2 | 2 | $(CH_2)_2$ | H | $CH_3$ | HCl (1/1) | 118-120 |
| 65. | 4-F-phenyl | O | $(CH_2)_2$ | 2 | 2 | bond | H | $CH_3$ | base | 135-137 |
| 66. | 4-Cl-phenyl | O | $(CH_2)_2$ | 2 | 2 | bond | H | $CH_3$ | base | 141-145 |
| 67. | (2-Cl,3-Cl)-phenyl | O | $(CH_2)_2$ | 2 | 2 | bond | H | $CH_3$ | base | 128-130 |
| 68. | (2-Cl,4-Cl)-phenyl | O | $(CH_2)_2$ | 2 | 2 | bond | H | $CH_3$ | base | 115-119 |

TABLE 1-continued (I)

$$R_1-G-[A]_m-N\underset{(\phantom{CH_2})_n}{\overset{(\phantom{CH_2})_o}{\diagup\hspace{-0.5em}\diagdown}}B-NH-C(=O)-O-CH(R_2)-C(=O)-NH-R_3$$

| Cpd | $R_1$ | G | $[A]_m$ | n | o | B | $R_2$ | $R_3$ | Base or salt | M.P. (° C.) |
|---|---|---|---|---|---|---|---|---|---|---|
| 69. | (2-Cl,4-Cl)-phenyl | O | CH(CH$_3$)CH$_2$ | 2 | 2 | bond | H | CH$_3$ | HCl (1/1) | 141-143 |
| 70. | (3-Cl,4-Cl)-phenyl | O | (CH$_2$)$_2$ | 2 | 2 | bond | H | CH$_3$ | base | 146-148 |
| 71. | 4-Cl-naphthalen-1-yl | O | (CH$_2$)$_2$ | 2 | 2 | bond | H | CH$_2$ | base | 136-140 |
| 72. | 4-Cl-naphthalen-1-yl | O | (CH$_2$)$_2$ | 2 | 2 | bond | H | H | base | 141-143 |
| 73. | quinolin-5-yl | O | (CH$_2$)$_2$ | 2 | 2 | bond | H | CH$_2$ | base | 140-142 |
| 74. | isoquinolin-5-yl | O | (CH$_2$)$_2$ | 2 | 2 | bond | H | CH$_3$ | base | 149-153 |
| 75. | 4-Cl-phenyl | O | (CH$_2$)$_2$ | 2 | 2 | CH$_2$ | H | CH$_3$ | base | 115-119 |
| 76. | (2-Cl,3-Cl)-phenyl | O | (CH$_2$)$_2$ | 2 | 2 | CH$_2$ | H | CH$_2$ | base | 117-119 |
| 77. | (2-Cl,4-Cl)-phenyl | O | (CH$_2$)$_2$ | 2 | 2 | CH$_2$ | H | CH$_3$ | HCl (1/1) | 137-139 |
| 78. | (2-Cl,4-Cl)-phenyl | O | CH(CH$_3$)CH$_2$ | 2 | 2 | CH$_2$ | H | CH$_3$ | HCl (1/1) | 194-196 |
| 79. | (3-Cl,4-Cl)-phenyl | O | (CH$_2$)$_2$ | 2 | 2 | CH$_2$ | H | CH$_3$ | base | 98-100 |
| 80. | 4-Cl-naphthalen-1-yl | O | (CH$_2$)$_2$ | 2 | 2 | CH$_2$ | H | CH$_3$ | base | 116-120 |
| 81. | quinolin-5-yl | O | (CH$_2$)$_2$ | 2 | 2 | CH$_2$ | H | CH$_3$ | HCl (1/1) | 220-224 |
| 82. | isoquinolin-5-yl | O | (CH$_2$)$_2$ | 2 | 2 | CH$_2$ | H | CH$_3$ | HCl (1/1) | 74-78 |
| 83. | 4-F-phenyl | O | (CH$_2$)$_2$ | 2 | 2 | (CH$_2$)$_2$ | H | CH$_3$ | base | 125-129 |
| 84. | 4-Cl-phenyl | O | (CH$_2$)$_2$ | 2 | 2 | (CH$_2$)$_2$ | H | CH$_3$ | base | 109-113 |
| 85. | 4-Cl-phenyl | O | (CH$_2$)$_3$ | 2 | 2 | bond | H | CH$_3$ | base | 133-137 |
| 86. | 4-F-phenyl | O | (CH$_2$)$_2$ | 1 | 2 | CH$_2$ | H | CH$_3$ | HCl (1/1) | 354* |
| 87. | 4-Cl-phenyl | O | (CH$_2$)$_2$ | 1 | 2 | CH$_2$ | H | CH$_3$ | base | 67-69 |
| 88. | 3-(4-F-phenyloxy)-phenyl | bond | CH$_2$ | 2 | 2 | bond | H | CH$_3$ | base | 107-109 |
| 89. | 5-(4-Cl-phenyl)iso-xazol-3-yl | bond | (CH$_2$)$_3$ | 2 | 2 | bond | H | CH$_3$ | base | 151-153 |
| 90. | 3-CF$_3$O-phenyl | bond | CH$_2$ | 2 | 2 | CH$_2$ | H | CH$_3$ | base | 73-75 |
| 91. | 4-CF$_3$O-phenyl | bond | CH$_2$ | 2 | 2 | CH$_2$ | H | CH$_3$ | base | 104-106 |
| 92. | 3-(pyrimidin-2-yloxy)-phenyl | bond | CH$_2$ | 2 | 2 | CH$_2$ | H | CH$_3$ | HCl (1/1) | 196-200 |
| 93. | 3-(4-Cl-phenyl)iso-xazol-5-yl | bond | CH$_2$ | 2 | 2 | CH$_2$ | H | CH$_3$ | base | 148-150 |
| 94. | 5-(4-Cl-phenyl)-1,3-oxazol-2-yl | bond | CH$_2$ | 2 | 2 | CH$_2$ | H | CH$_2$ | base | 143-145 |
| 95. | 4-(4-CF$_3$-phenyl)-1,3-thiazol-2-yl | bond | CH$_2$ | 2 | 2 | CH$_2$ | H | CH$_3$ | base | 172-174 |
| 96. | 5-(4-Cl-phenyl)iso-xazol-3-yl | bond | (CH$_2$)$_2$ | 2 | 2 | CH$_2$ | H | CH$_2$ | base | 165-167 |

TABLE 1-continued

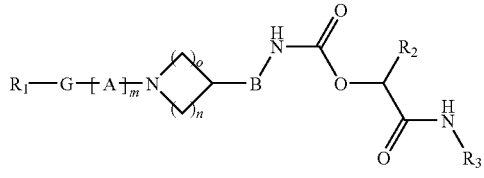

(I)

| Cpd | R₁ | G | [A]m | n | o | B | R₂ | R₃ | Base or salt | M.P. (° C.) |
|---|---|---|---|---|---|---|---|---|---|---|
| 97. | 3-(4-Cl-phenyl)isoxazol-5-yl | bond | $(CH_2)_2$ | 2 | 2 | $CH_2$ | H | $CH_3$ | base | 146-148 |
| 98. | 3-(4-Cl-phenyl)isoxazol-5-yl | bond | $(CH_2)_3$ | 2 | 2 | $CH_2$ | H | $CH_3$ | base | 134-136 |
| 99. | 5-(4-Cl-phenylisoxazol-3-yl | bond | $(CH_2)_3$ | 2 | 2 | $CH_2$ | H | $CH_3$ | base | 160-162 |
| 100 | (2-Cl,4-F)-phenyl | bond | $CH_2$ | 2 | 2 | $(CH_2)_2$ | H | $CH_3$ | base | 108-110 |
| 101 | (3-Cl,4-F)-phenyl | bond | $CH_2$ | 2 | 2 | $(CH_2)_2$ | H | $CH_3$ | base | 112-114 |
| 102 | (3-CN,5-F)-phenyl | bond | $CH_2$ | 2 | 2 | $(CH_2)_2$ | H | $CH_3$ | base | 132-134 |
| 103 | 3-(4-F-phenyloxy)-phenyl | bond | $CH_2$ | 2 | 2 | $(CH_2)_2$ | H | $CH_3$ | base | 79-81 |
| 104 | 3-(4-Cl-phenyl)isoxazol-5-yl | bond | $CH_2$ | 2 | 2 | $(CH_2)_2$ | H | $CH_3$ | base | 169-171 |
| 105 | 5-(4-Cl-phenyl)-1,3-oxazol-2-yl | bond | $CH_2$ | 2 | 2 | $(CH_2)_2$ | H | $CH_3$ | base | 124-126 |
| 106 | 4-(4-CF₃-phenyl)-1,3-thiazol-2-yl | bond | $CH_2$ | 2 | 2 | $(CH_2)_2$ | H | $CH_3$ | base | 161-163 |
| 107 | (2-Cl,4-F)-phenyl | bond | $CH(CH_3)$ | 2 | 2 | $CH_2$ | H | $CH_3$ | HCl (1/1) | 386* |
| 108 | 3-(4-Cl-phenyloxy)-phenyl | bond | $CH(CH_3)$ | 2 | 2 | $CH_2$ | H | $CH_3$ | HCl (1/1) | 130-134 |
| 109 | [2-Cl,3-(4-Cl-phenyloxy)]phenyl | bond | $CH(CH_3)_2$ | 2 | 2 | $CH_2$ | H | $CH_3$ | base | 115-119 |
| 110 | 3-CF₃O-phenyl | bond | $CH(CH_3)_2$ | 2 | 2 | $(CH_2)_2$ | H | $CH_3$ | HCl (1/1) | 169-171 |
| 111 | (2-Cl,4-F)-phenyl | bond | $CH(CH_3)_2$ | 2 | 2 | $(CH_2)_2$ | H | $CH_3$ | HCl (1/1) | 400* |
| 112 | 4-Cl-phenyl | bond | C≡C—$(CH_2)_2$ | 2 | 2 | bond | H | $CH_3$ | base | 189-191 |
| 113 | 4-Cl-phenyl | bond | C≡C—$(CH_2)_3$ | 2 | 2 | bond | H | $CH_3$ | base | 137-139 |
| 114 | (2-Cl,5-Cl)-phenyl | bond | C≡C—$(CH_2)_3$ | 2 | 2 | bond | H | $CH_3$ | base | 426* |
| 115 | (2-Cl,4-F)-phenyl | bond | C≡C—$(CH_2)_3$ | 2 | 2 | bond | H | $CH_3$ | base | 410* |
| 116 | 4-Cl-phenyl | bond | C≡C—$(CH_2)_2$ | 2 | 2 | $CH_2$ | H | $CH_3$ | base | 151-153 |
| 117 | (2-Cl,3-Cl)-phenyl | O | $(CH_2)_2$ | 1 | 1 | bond | H | $CH_3$ | base | 138-140 |
| 118 | (2-F,4-Cl)-phenyl | bond | C≡C—$(CH_2)_2$ | 2 | 2 | $CH_2$ | H | $CH_3$ | base | 144-146 |
| 119 | (2-Cl,5-Cl)-phenyl | bond | C≡C—$(CH_2)_2$ | 2 | 2 | $CH_2$ | H | $CH_3$ | base | 128-130 |
| 120 | 3-(4-Cl-phenyl)isoxazol-5-yl | bond | $(CH_2)_2$ | 2 | 2 | $(CH_2)_2$ | H | $CH_3$ | base | 135-137 |
| 121 | 3-t-BuO-phenyl | bond | $CH_2$ | 2 | 2 | $CH_2$ | H | $CH_3$ | base | 392* |
| 122 | 3-t-BuO-phenyl | bond | $CH_2$ | 2 | 2 | $(CH_2)_2$ | H | $CH_3$ | base | 66-70 |

*M + H

The compounds of the invention were subjected to pharmacological tests allowing determination of their inhibitory effect on the enzyme FAAH (fatty acid amide hydrolase).

The inhibitory activity was demonstrated in a radioenzymatic assay based on measuring the product of hydrolysis ([1-$^3$H]ethanolamine) of anandamide [1-$^3$H ethanolamine] by FAAH (*Life Sciences* (1995), 56, 1999-2005 and *Journal of Pharmacology and Experimental Therapeutics* (1997), 283, 729-734). Accordingly, mouse brains (minus the cerebellum) are removed and stored at −80° C. Membrane homogenates are prepared at the time of use by homogenizing the tissues in a Polytron in a 10 mM Tris-HCl buffer (pH 8.0) containing 150 mM NaCl and 1 mM EDTA. The enzymatic reaction is subsequently conducted in 70 μl of buffer containing bovine serum albumin without fatty acids (1 mg/ml). In succession the test compounds, at various concentrations, anandamide [1-$^3$H ethanolamine] (specific activity: 15-20 Ci/mmol) diluted to 10 μM with cold anandamide, and the membrane preparation (400 μg of frozen tissue per assay) are added. After 15 minutes at 25° C., the enzymatic reaction is terminated by adding 140 μl of chloroform/methanol (2:1). The mixture is stirred for 10 minutes and then centrifuged for 15 minutes at 3500 g. An aliquot (30 μl) of the aqueous phase containing the ethanolamine [1-$^3$H] is counted by liquid scintillation.

Under these conditions the most active compounds of the invention exhibit $IC_{50}$ values (concentration inhibiting by 50% the control enzymatic activity of FAAH) of between 0.001 and 1 μM.

Table 2 below presents the $IC_{50}$ values of some compounds according to the invention.

TABLE 2

| Compound | $IC_{50}$ |
|---|---|
| 25 | 0.225 μM |
| 77 | 0.049 μM |

It is therefore apparent that the compounds according to the invention have an inhibitory activity on the FAAH enzyme.

The in vivo activity of the compounds of the invention was evaluated in an analgesia test.

Accordingly, intraperitoneal (i.p.) administration of PBQ (phenylbenzoquinone, 2 mg/kg in a 0.9% sodium chloride solution containing 5% of ethanol) to male OF1 mice weighing 25 to 30 g causes abdominal stretches, on average 30 twists or contractions during the period from 5 to 15 minutes after injection. The test compounds are administered orally (p.o.) or intraperitoneally (i.p.) in suspension in Tween 80 at 0.5%, 60 minutes or 120 minutes before the administration of PBQ. Under these conditions the most potent compounds of the invention reduce by 35% to 70% the number of stretches induced by PBQ, within a dose range of between 1 and 30 mg/kg.

For example, compound 26 of the table reduces by 56% the number of stretches induced by PBQ, at a dose of 10 mg/kg p.o. at 120 minutes.

As discussed earlier, the enzyme FAAH (*Chemistry and Physics of Lipids*, (2000), 108, 107-121) catalyses the hydrolysis of endogenous derivatives of amides and of esters of various fatty acids such as N-arachidonoylethanolamine (anandamide), N-palmitoylethanolamine, N-oleoylethanolamine, oleamide or 2-arachidonoylglycerol. These derivatives exert various pharmacological activities by interacting, inter alia, with cannabinoid and vanilloid receptors.

The compounds of the invention block this degradation pathway and increase the tissue level of these endogenous substances. They can be used in this respect in the prevention and treatment of pathologies in which endogenous cannabinoids and/or any other substrates metabolized by the FAAH enzyme are involved.

The use of a compound of formula (I), in the base or pharmaceutically acceptable salt, hydrate or solvate form, in the preparation of a medicament intended to treat the above-mentioned pathologies forms an integral part of the invention.

Another subject-matter of the invention is medicaments which comprise a compound of formula (I) or a pharmaceutically acceptable salt, hydrate or solvate of the compound of formula (I). These medicaments are used in therapeutics, in particular in the treatment of the above-mentioned pathologies.

According to another of its aspects, the present invention relates to pharmaceutical compositions including, as active principle, at least at least one compound according to the invention. These pharmaceutical compositions comprise an effective dose of a compound according to the invention or a pharmaceutically acceptable salt, hydrate or solvate of the said compound and optionally one or more pharmaceutically acceptable excipients.

The said excipients are chosen, depending on the pharmaceutical form and the method of administration desired, from the usual excipients which are known to a person skilled in the art such as those selected from the group comprising carbohydrates, cellulose and cellulose derivatives, starches, synthetic and natural polymers, sugars and sugar alcohols, gelatin, lipids, fats, lubricants and mixtures thereof.

In the pharmaceutical compositions of the present invention for oral, sublingual, subcutaneous, intramuscular, intravenous, topical, local, intrathecal, intranasal, transdermal, pulmonary, ocular or rectal administration, the active principle of formula (I) above, or its salt, solvate or hydrate where appropriate, may be administered in a single-dose administration form, in a mixture with conventional pharmaceutical excipients, to animals and to humans for the prophylaxis or treatment of the above disorders or diseases.

The unit-dose administration forms which are appropriate include oral forms such as tablets, soft or hard gelatine capsules, powders, granules, chewing gums and oral solutions or suspensions, forms for sublingual, buccal, intratracheal, intraocular and intranasal administration, and for administration by inhalation, forms for subcutaneous, intramuscular or intravenous administration and forms for rectal or vaginal administration. For topical application the compounds according to the invention may be used in creams, ointments or lotions.

By way of example a single-dose administration form of a compound according to the invention in tablet form may comprise the following components:

| | |
|---|---|
| A compound according to the invention | 50.0 mg |
| Mannitol | 223.75 mg |
| Croscaramellose sodium | 6.0 mg |
| Maize starch | 15.0 mg |
| Hydroxypropylmethylcellulose | 2.25 mg |
| Magnesium stearate | 3.0 mg |

The said single-dose forms contain a dose permitting daily administration of 0.01 to 20 mg of active principle per kg of body weight, depending on the pharmaceutical form.

There may be particular cases in which higher or lower dosages are appropriate; such dosages also belong to the invention. In accordance with customary practice, the dosage appropriate to each patient is determined by the doctor according to the mode of administration, the weight and the response of the said patient.

According to another of its aspects the invention also provides a method of treating the pathologies indicated above, which comprises administering an effective dose of a compound according to the invention, one of its pharmaceutically acceptable salts, a solvate or a hydrate of the said compound.

What is claimed is:

1. A compound of the formula (I):

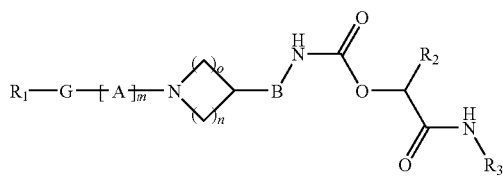

(I)

in which
m represents an integer from 1 to 4;
n represents an integer 2;
o represents an integer 2;
A is selected from one or more groups X, Y and/or Z;
  X represents a methylene group optionally substituted by one or two $C_{1-6}$ alkyl, $C_{3-7}$ cycloalkyl or $C_{3-7}$ cycloalkyl-$C_{1-3}$ alkylene groups;
  Y represents either a $C_2$ alkenylene group optionally substituted by one or two $C_{1-6}$ alkyl, $C_{3-7}$ cycloalkyl or $C_{3-7}$ cycloalkyl-$C_{1-3}$ alkylene groups, or a $C_2$ alkynylene group;
  Z represents a group of formula:

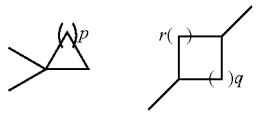

wherein p represents an integer from 1 to 5;
  q and r represent integers and are defined such that r+q is a number from 1 to 5;
B represents a covalent bond or a $C_{1-6}$ alkylene group;
G represents a covalent bond, an oxygen or sulphur atom or a —CH(OH)—, CO, SO or $SO_2$ group;
$R_1$ represents a group $R_4$ optionally substituted by one or more groups $R_5$ and/or $R_6$;
$R_4$ represents a group selected from a furanyl, pyrrolyl, thienyl, oxazolyl, isoxazolyl, thiazolyl, isothiazolyl, imidazolyl, pyrazolyl, thiadiazolyl, isothiadiazolyl, oxadiazolyl, thiadiazolyl, triazolyl, tetrazolyl, phenyl, pyridinyl, pyridazinyl, pyrimidinyl, pyrazinyl, triazinyl, naphthalenyl, quinolinyl, tetrahydroquinolinyl, isoquinolinyl, tetrahydroisoquinolinyl, phthalazinyl, quinazolinyl, quinoxalinyl, cinnolinyl, naphthyridinyl, imidazopyrimidinyl, thienopyrimidinyl, benzofuranyl, dihydrobenzo-furanyl, benzothienyl, dihydrobenzothienyl, benzimidazolyl, benzoxazolyl, benzisoxazolyl, benzothiazolyl, benzisothiazolyl, indolyl, isoindolyl, indazolyl, pyrrolopyridinyl, furopyridinyl, dihydrofuropyridinyl, thienopyridinyl, dihydrothienopyridinyl, imidazopyridinyl, pyrazolopyridinyl, oxazolopyridinyl, isoxazolopyridinyl, thiazolopyridinyl;
$R_5$ represents a halogen atom, a cyano, nitro, hydroxyl, $C_{1-6}$ alkyl, $C_{1-6}$ alkoxy, $C_{1-6}$ thioalkyl, $C_{1-6}$ fluoroalkyl, $C_{1-6}$ fluoroalkoxy, $C_{1-6}$ fluorothioalkyl, $C_{3-7}$ cycloalkyl or $C_{3-7}$ cycloalkyl-$C_{1-3}$ alkylene group or a group $NR_7R_8$, $NR_7COR_8$, $NR_7CO_2R_8$, $NR_7SO_2R_8$, $COR_7$, $CO_2R_7$, $CONR_7R_8$, $SO_2R_7$, $SO_2NR_7R_8$ or —O—($C_{1-3}$ alkylene)—O—;
$R_6$ represents a phenyl, phenyloxy, benzyloxy, pyridinyl, pyrazinyl, pyridazinyl, pyrimidinyl or pyrimidinyloxy group; it being possible for the group or groups $R_6$ to be substituted by one or more groups $R_5$ identical to or different from one another;
$R_7$ and $R_8$ represent independently of one another a hydrogen atom or a $C_{1-6}$ alkyl group, or, with the atom or atoms which carry them, form a ring selected from an azetidine, pyrrolidine, piperidine, morpholine, thiomorpholine, azepine or piperazine ring, this ring being optionally substituted by a $C_{1-6}$ alkyl or benzyl group;
$R_2$ represents a hydrogen atom or a $C_{1-6}$ alkyl group; and
$R_3$ represents a hydrogen atom or a $C_{1-6}$ alkyl, $C_{3-7}$ cycloalkyl or $C_{3-7}$ cycloalkyl-$C_{1-3}$ alkylene group;
or an addition salt thereof.

2. The compound of formula (I) as recited in claim 1, wherein:
m represents an integer from 1 to 4;
n represents an integer 2;
o represents an integer 2;
A is selected from one or more groups X and/or Y;
  X represents a methylene group optionally substituted by one or two $C_{1-6}$ alkyl groups;
  Y represents a $C_2$ alkynylene group;
B represents a covalent bond or a $C_{1-6}$ alkylene group;
G represents a covalent bond or an oxygen atom;
$R_1$ represents a group $R_4$ optionally substituted by one or more groups $R_5$ and/or $R_6$;
  $R_4$ represents a group selected from an oxazolyl, isoxazolyl, thiazolyl, phenyl, pyridinyl, naphthalenyl, quinolinyl, isoquinolinyl;
  $R_5$ represents a halogen atom, a cyano group, a group $NR_7R_8$, or a $C_{1-6}$ alkyl group, a $C_{1-6}$ alkoxy group, a $C_{1-6}$ fluoroalkyl group or a $C_{1-6}$ fluoroalkoxy group;
  $R_6$ represents a phenyl, phenyloxy or pyrimidinyloxy group; it being possible for the group or groups $R_6$ to be substituted by one or more groups $R_5$ identical to or different from one another;
  $R_7$ and $R_8$ represent independently of one another a $C_{1-6}$ alkyl group;
$R_2$ represents a hydrogen atom or a $C_{1-6}$ alkyl group; and
$R_3$ represents a hydrogen atom or a $C_{1-6}$ alkyl, $C_{3-7}$ cycloalkyl or $C_{3-7}$ cycloalkyl-$C_{1-3}$ alkylene group;
or an addition salt thereof.

3. The compound of formula (I) as recited in claim 2 wherein:
m represents an integer 1 or 2;
or an addition salt thereof.

4. The compound of formula (I) as recited in claim 3, wherein;
n is 2; and
o is 2;
or an addition salt thereof.

5. The compound of formula (I) as recited in claim 4 wherein:
$R_1$ represents a group $R_4$ optionally substituted by one or more groups $R_5$ and/or $R_6$;

$R_4$ represents a group selected from an oxazolyl, isoxazolyl, phenyl or naphthalenyl;

$R_5$ represents a halogen atom, a cyano group, a group $NR_7R_8$, a $C_{1-6}$ alkyl group, a $C_{1-6}$ alkoxy group, a $C_{1-6}$ fluoroalkyl group, or a $C_{1-6}$ fluoroalkoxy group;

$R_6$ represents a phenyl, phenyloxy or pyrimidinyloxy group; it being possible for the group or groups $R_6$ to be substituted by one or more groups $R_5$ identical to or different from one another; and $R_7$ and $R_8$ represent independently of one another a $C_{1-6}$ alkyl group;

or an addition salt thereof.

6. The compound of formula (I) as set forth in claim 5 wherein:

$R_2$ represents a hydrogen atom;

$R_3$ represents a hydrogen atom or a $C_{1-6}$ alkyl group;

or an addition salt thereof.

7. A process for the preparation of a compound of formula (I) as recited in claim 1, comprising the conversion of the oxazolidine-dione of general formula (IIa):

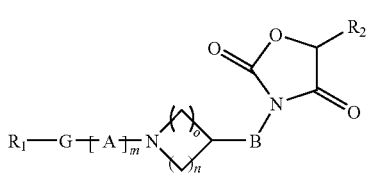

(IIa)

by aminolysis using an amine of general formula $R_3NH_2$ in which A, B, G, $R_1$, $R_2$, $R_3$, m, n and o are as defined in claim 1.

8. A process for the preparation of a compound of formula (I) as recited in claim 1, comprising the conversion of the carbamate-amide derivative of general formula (Ia):

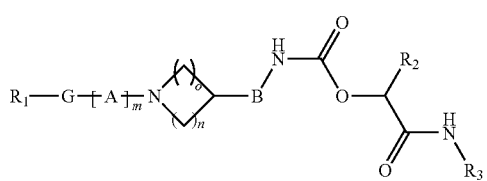

(Ia)

in which B, $R_2$, $R_3$, n and o are as defined in claim 1, by reaction with a derivative of general formula (III):

(III)

in which W represents a mesylate or tosylate group or a chlorine, bromine or iodine atom and m, G, A and $R_1$ are as defined in claim 1.

9. A pharmaceutical composition comprising at least one compound of formula (I):

(I)

wherein $R_1$, $R_2$, $R_3$, A, B, G, m, n, and o are as defined in claim 1 or a pharmaceutically acceptable salt thereof in combination with one or more pharmaceutically acceptable excipients.

\* \* \* \* \*

UNITED STATES PATENT AND TRADEMARK OFFICE
CERTIFICATE OF CORRECTION

PATENT NO. : 7,781,590 B2  
APPLICATION NO. : 11/465825  
DATED : August 24, 2010  
INVENTOR(S) : Ahmed Abouabdellah et al.

Page 1 of 1

It is certified that error appears in the above-identified patent and that said Letters Patent is hereby corrected as shown below:

In column 19-20, line 25, delete "eli 2" and insert -- $CH_2$ --, therefor.

In column 21-22, line 15, delete "phenyloxy" and insert -- phenyloxy- --, therefor.

In column 21-22, line 40, delete "phenyloxy" and insert -- phenyloxy- --, therefor.

In column 23-24, line 10, delete "$CH_2$" and insert -- $CH_3$ --, therefor.

In column 23-24, line 16, delete "$CH_2$" and insert -- $CH_3$ --, therefor.

In column 23-24, line 21, delete "$CH_2$" and insert -- $CH_3$ --, therefor.

In column 23-24, line 59, delete "$CH_2$" and insert -- $CH_3$ --, therefor.

In column 23-24, line 65, delete "$CH_2$" and insert -- $CH_3$ --, therefor.

Signed and Sealed this  
Twenty-sixth Day of July, 2011

David J. Kappos  
*Director of the United States Patent and Trademark Office*